United States Patent
Miura et al.

(10) Patent No.: US 7,680,305 B2
(45) Date of Patent: Mar. 16, 2010

(54) VEIN AUTHENTICATION DEVICE

(75) Inventors: Naoto Miura, Kokubunji (JP); Akio Nagasaka, Kokubunji (JP); Takafumi Miyatake, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 823 days.

(21) Appl. No.: 10/586,837

(22) PCT Filed: Jun. 13, 2005

(86) PCT No.: PCT/JP2005/011184
§ 371 (c)(1),
(2), (4) Date: Jul. 21, 2006

(87) PCT Pub. No.: WO2006/134669
PCT Pub. Date: Dec. 21, 2006

(65) Prior Publication Data
US 2008/0112600 A1  May 15, 2008

(51) Int. Cl.
*G06K 9/00* (2006.01)
*G06K 19/00* (2006.01)

(52) U.S. Cl. .................. 382/115; 382/124; 340/5.52

(58) Field of Classification Search ......... 382/115–118, 382/124, 126, 127, 313, 314, 315, 125; 340/5.53, 340/5.83, 5.82, 5.52, 356; 358/497, 486; 250/234; 713/186; 235/380; 705/44
See application file for complete search history.

(56) References Cited

U.S. PATENT DOCUMENTS

| | | | |
|---|---|---|---|
| 6,993,160 B2 | 1/2006 | Miura et al. | |
| 7,181,048 B2 * | 2/2007 | Blume | 382/115 |
| 7,273,170 B2 * | 9/2007 | Katsumata et al. | 235/382 |
| 7,327,561 B2 * | 2/2008 | Chen | 361/679.27 |
| 7,327,861 B2 * | 2/2008 | Choshi et al. | 382/124 |
| 7,359,531 B2 * | 4/2008 | Endoh et al. | 382/115 |
| 7,376,839 B2 * | 5/2008 | Carta et al. | 713/185 |
| 2002/0028004 A1 | 3/2002 | Miura et al. | |
| 2002/0067845 A1 | 6/2002 | Griffis | |
| 2003/0086588 A1 | 5/2003 | Shinada et al. | |
| 2003/0103686 A1 | 6/2003 | Ogura | |
| 2004/0184641 A1 | 9/2004 | Nagasaka et al. | |
| 2005/0047632 A1 | 3/2005 | Miura et al. | |

(Continued)

FOREIGN PATENT DOCUMENTS

EP    976 897 A1    2/2000

(Continued)

*Primary Examiner*—Sheela C Chawan
(74) *Attorney, Agent, or Firm*—Mattingly & Malur, P.C.

(57) ABSTRACT

Provided in this invention is a vein authentication device comprising: an interface on which a part of a living body; one or more light sources for emitting infrared light; an image pickup unit for picking up a blood vessel image of the part of the living body using infrared light emitted from the light sources; an image computing unit for processing the blood vessel image picked up by the image pickup unit; and a light shielding unit for shielding infrared light emitted from the light sources and preventing the infrared light from traveling in an image pickup direction of the image pickup unit, wherein the interface has an opening opened in the image pickup direction of the image pickup unit, and wherein the light sources irradiates the part of the living body with infrared light from an image pickup side of the part of the living body.

12 Claims, 34 Drawing Sheets

U.S. PATENT DOCUMENTS

| | | |
|---|---|---|
| 2005/0148876 A1 | 7/2005 | Endoh et al. |
| 2006/0023919 A1* | 2/2006 | Okamura et al. ............ 382/115 |
| 2007/0058841 A1 | 3/2007 | Miura et al. |

FOREIGN PATENT DOCUMENTS

| | | |
|---|---|---|
| EP | 1 271 389 A2 | 1/2003 |
| EP | 1 376 465 A1 | 1/2004 |
| JP | 2001-184507 A | 7/2001 |
| JP | 2002-83300 | 3/2002 |
| JP | 2003-242492 A | 8/2003 |
| JP | 2004-086866 | 3/2004 |
| JP | 2004-131927 | 4/2004 |
| JP | 2004-265269 | 9/2004 |
| JP | 2004-265369 A | 9/2004 |
| WO | 00/39743 A1 | 7/2000 |
| WO | 00/39744 A1 | 7/2000 |
| WO | 02/099393 | 12/2002 |
| WO | 2005/013183 A2 | 2/2005 |
| WO | WO 2006/134669 A1 | 12/2006 |

* cited by examiner

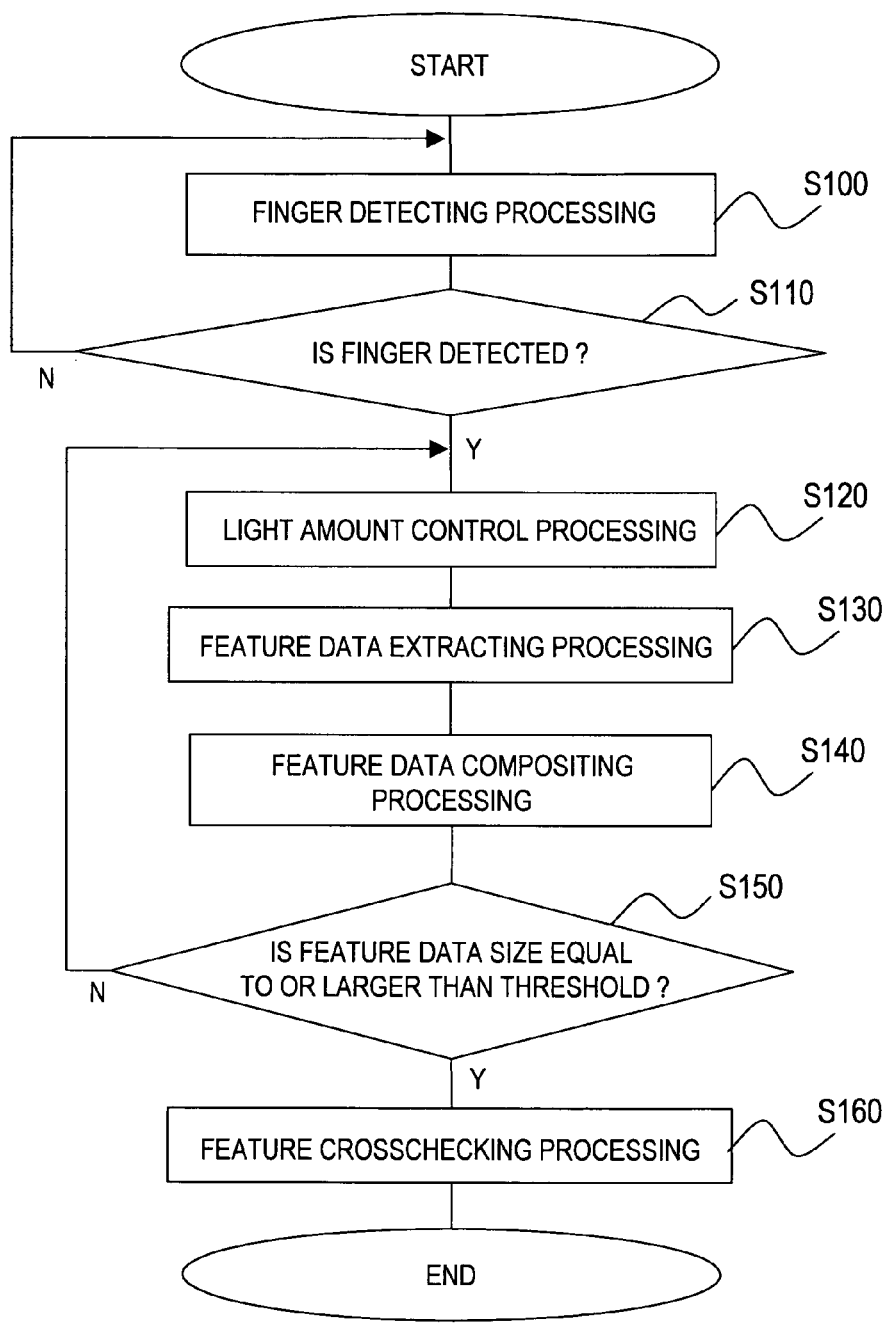

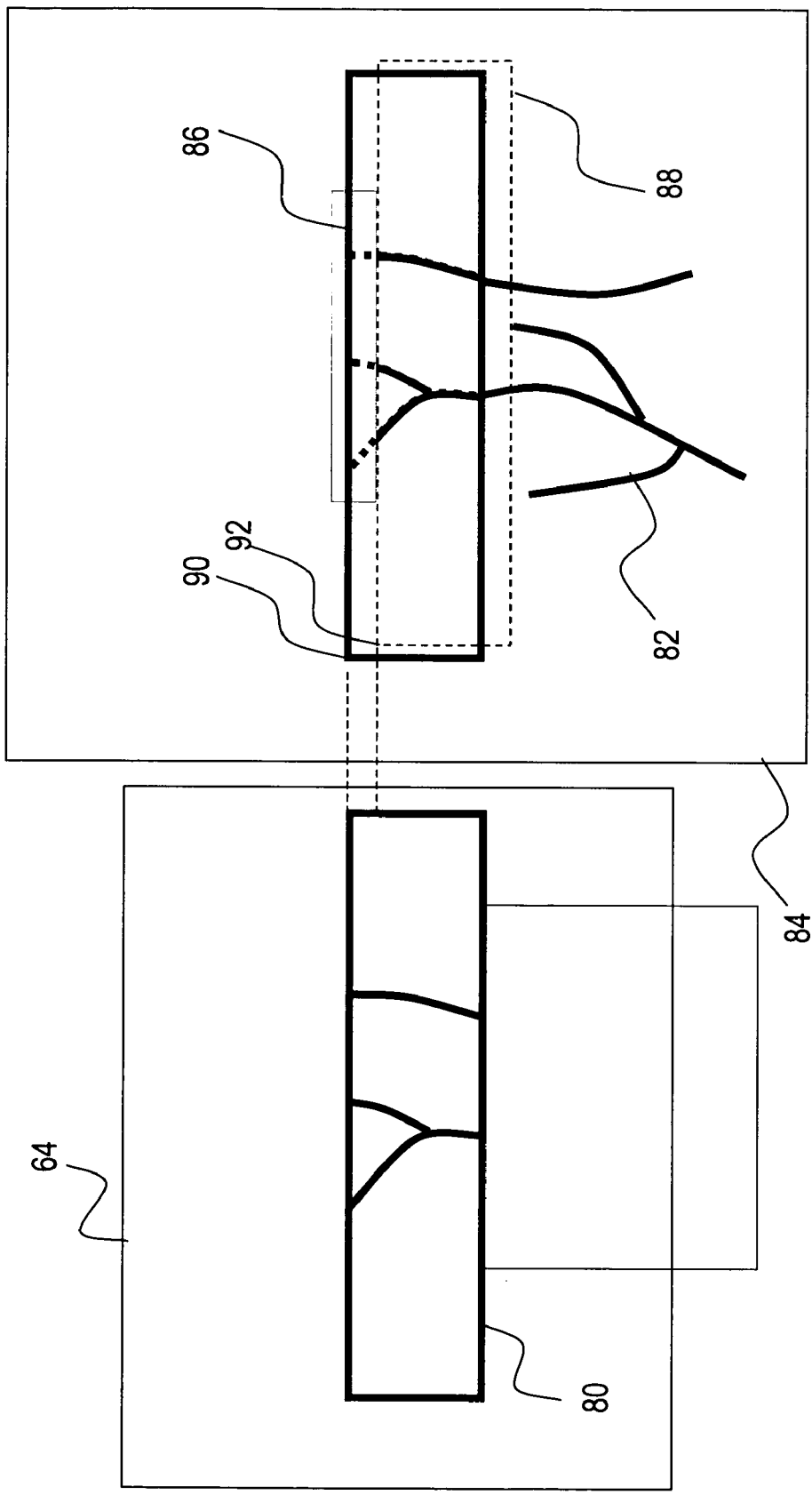

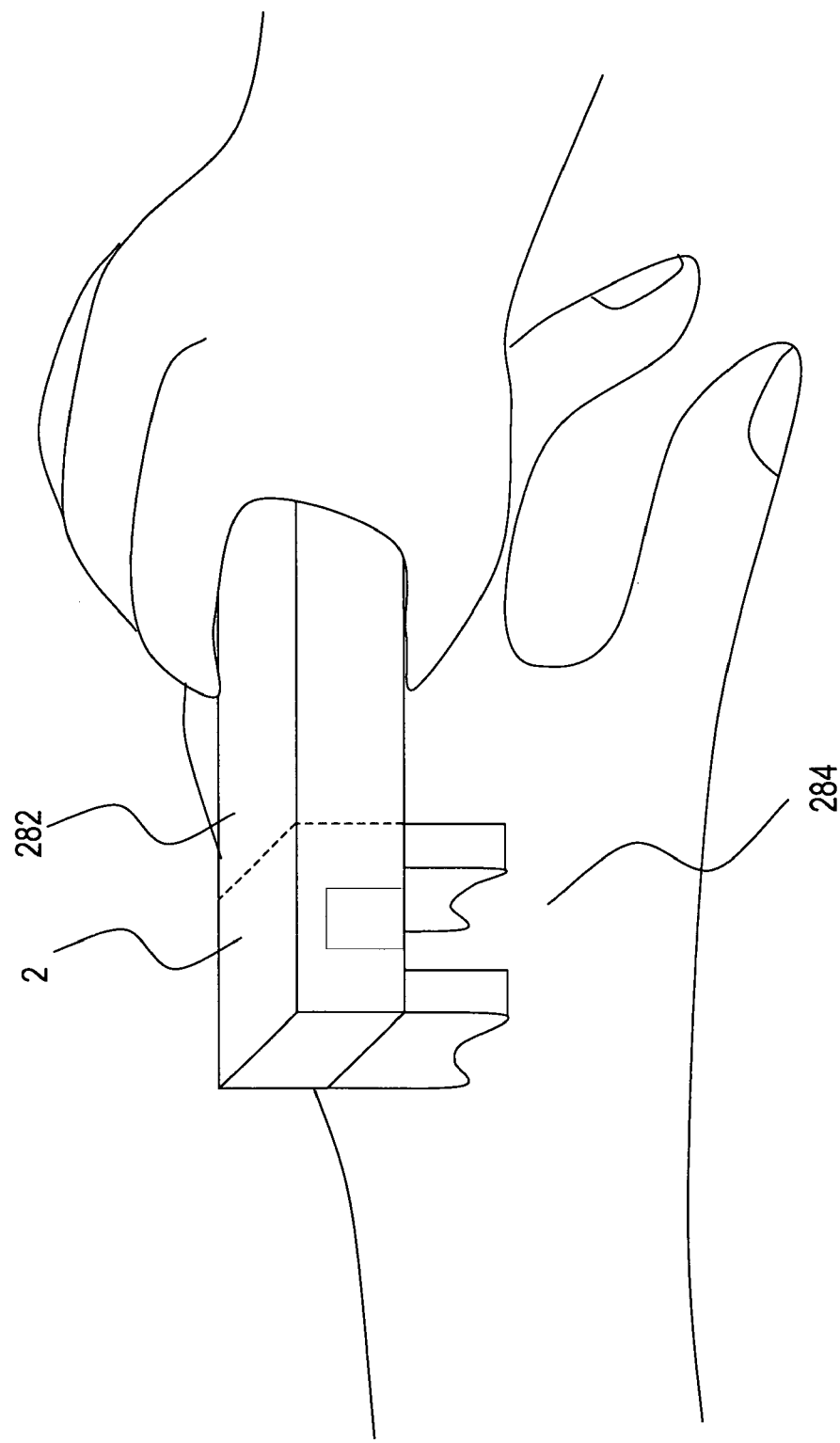

VEIN AUTHENTICATION DEVICE

TECHNICAL FIELD

This invention relates to an authentication device for authenticating individuals, and more specifically, to an authentication technique using venous information of a living body.

BACKGROUND ART

Security of personal information is gaining greater importance in recent years. Biometrics authentication is attracting attention as individual authentication technology for ensuring security. Biometrics authentication is authentication technology that uses physiological information of a person, and is excellent in terms of convenience and preservation of confidentiality.

Examples of known conventional biometrics authentication technology include authentication using a fingerprint, iris, voice, face, or vein on the back of a hand or on the palm side of a finger. In vein biometric authentication, in particular, a user only has to present a part of his/her body such as a hand or a finger to an authentication device for authentication. Vein biometric authentication (i.e., vein authentication devices) therefore causes less reluctance in users. Furthermore, utilizing in vivo information, vein authentication devices are highly fraud-proof.

The description given below focuses on finger vein authentication devices.

A finger vein authentication device first irradiates a finger with infrared light, which is scattered inside the finger and then transmitted to the outside. The finger vein authentication device picks up the infrared light transmitted through the palm side of the finger.

Since hemoglobin in blood absorbs infrared light more than its surrounding tissues, the image picked up by the finger vein authentication device is a visualization of blood vessels running under the skin on the palm side of the finger (i.e., finger veins) as a dark shadow pattern (i.e., finger vein pattern).

Features of the finger vein pattern are registered in the finger vein authentication device in advance.

For authentication, the finger vein authentication device picks up an image of the user's finger. The finger vein authentication device accomplishes individual authentication by obtaining a correlation between a finger vein pattern of the image picked up and the features registered in advance.

However, conventional finger vein authentication devices pick up an image of a finger inserted into the finger vein authentication devices. Therefore, users feel reluctant to insert a finger into the closed interior space of a finger vein authentication device.

A finger vein authentication device described in JP 2004-265269 A addresses this problem. This finger vein authentication device places a light source for irradiating a finger with infrared light on each side of a finger. A user can thus be authenticated by merely putting his/her finger on the device.

A drawback of this finger vein authentication device, which requires spaces flanking a finger to install the light sources, is that the device cannot be reduced in size.

WO 2002/099393 describes a flat-structured finger vein authentication device.

This finger vein authentication device has a light source set on the same plane as an image pickup device with respect to veins to be photographed.

DISCLOSURE OF THE INVENTION

A finger vein authentication device with a light source set on the same plane as an image pickup device undesirably picks up light that is reflected from the skin surface of a finger. Accordingly, the finger vein authentication device cannot pick up a clear image of a vein pattern.

This invention has been made in view of the aforementioned problems, and it is therefore an object of this invention to provide a vein authentication device that can pick up a clear vein pattern image and can be made small in size.

According to this invention, there is provided a vein authentication device, characterized in that the vein authentication device includes: an interface on which a living body whose image is to be picked up is placed; a light source for emitting infrared light; an image pickup unit for picking up a blood vessel image of the living body using light from the light source; and an image computing unit for processing the blood vessel image picked up by the image pickup unit, and in that: the interface has an opening opened in an image pickup direction of the image pickup unit; the light source irradiates the living body with infrared light from an image pickup side of the living body; and a light shielding unit is provided to shield infrared light radiated from the light source and prevent the infrared light from traveling in the image pickup direction.

The vein authentication device of this invention can pick up a clear image of a vein pattern, and further, can be made small in size.

BRIEF DESCRIPTION OF THE DRAWINGS

FIG. 7 is a flow chart for authentication processing that is executed by the authentication processing unit according to the first embodiment of this invention.

FIG. 9 is an explanatory diagram of feature data compositing processing of the authentication processing unit according to the first embodiment of this invention.

FIG. 20A shows a probe type authentication device according to a tenth embodiment of this invention.

BEST MODE FOR CARRYING OUT THE INVENTION

Embodiments of this invention will be described below with reference to drawings. In the embodiments of this patent application, a finger vein authentication device is described in particular, but this invention is also applicable to a case where a palm or other living body parts are read.

First Embodiment

Figure 1:
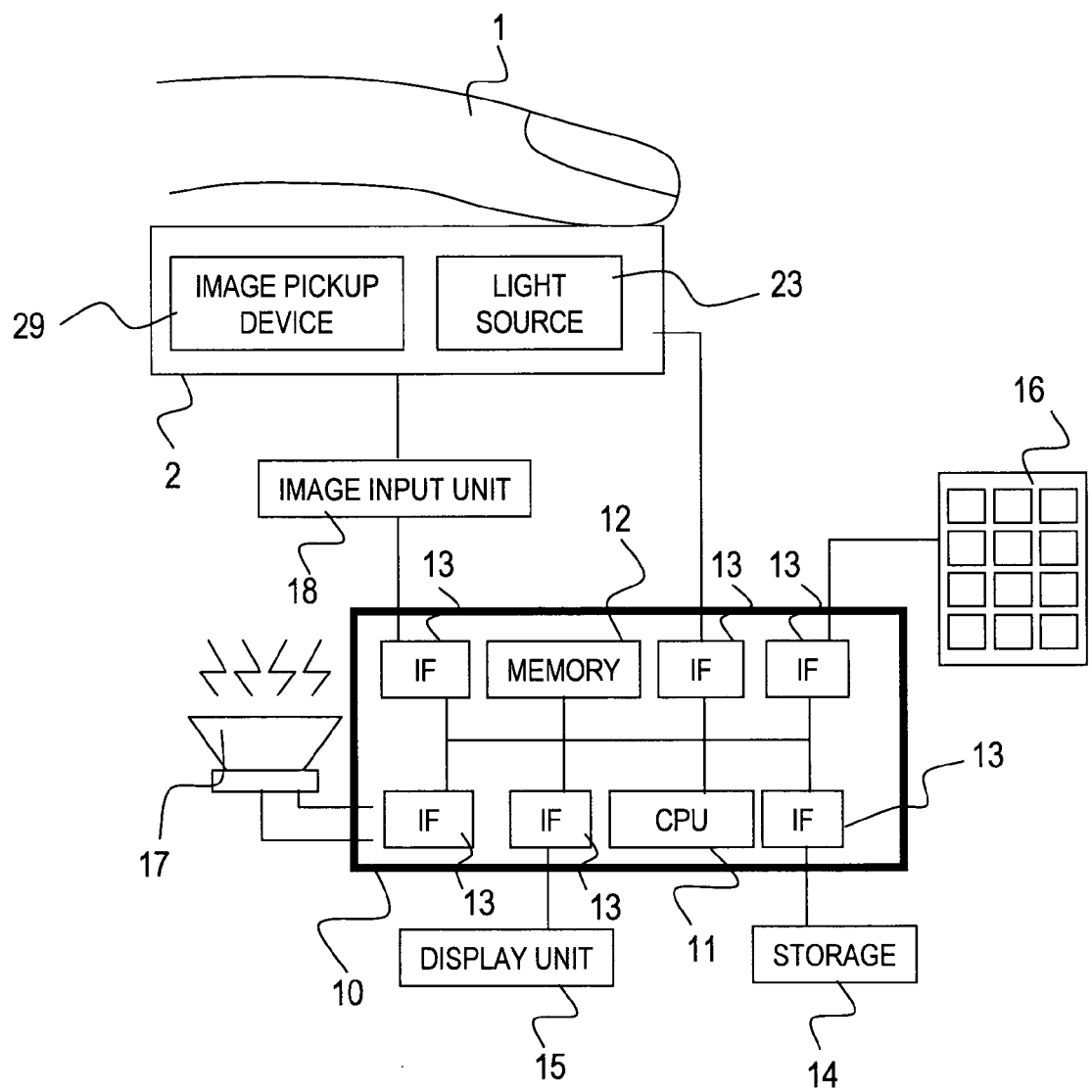
FIG. 1 is a configuration diagram of an authentication system according to a first embodiment of this invention.

FIG. 1 is a configuration diagram of an authentication system according to a first embodiment of this invention.

The authentication system contains an input device 2, an authentication processing unit 10, a storage 14, a display unit 15, an input unit 16, a speaker 17, and an image input unit 18.

The input device 2 will be described later with reference to FIGS. 3A, 3B, and 3C. The input device 2 contains a light source 23 and an image pickup device 29.

The light source 23 is, for example, an infrared LED, and irradiates a finger 1 placed on the input device 2 with infrared light. The image pickup device 29 picks up an image of the finger 1 placed on the input device 2.

The image input unit 18 inputs an image picked up by the image pickup device 29 of the input device 2 into the authentication processing unit 10.

The authentication processing unit 10 contains a CPU 11, a memory 12, and interfaces (IFs) 13.

The CPU 11 performs various types of processing by executing programs stored in the memory 12. The memory 12 stores programs executed by the CPU as will be described later with reference to FIG. 2. The memory 12 also temporarily stores an image entered by the image input unit 18.

The interfaces 13 are connected to devices external to the authentication processing unit 10. To be specific, the interfaces 13 are connected to the input device 2, the storage 14, the display unit 15, the input unit 16, the speaker 17, the image input unit 18, and others.

The storage 14 stores in advance user crosscheck data, which is information for verifying users such as finger vein pattern images. A finger vein pattern image is an image of blood vessels running under the skin surface on the palm side of a finger (i.e., finger veins) that is picked up as a dark shadow pattern.

The display unit 15 is, for example, a liquid crystal display, and displays information received from the authentication processing unit 10.

The input unit 16 is, for example, a keyboard, and sends information entered by a user to the authentication processing unit 10. The speaker 17 outputs, in audio, information received from the authentication processing unit 10.

Described below is authentication processing by an authentication system of this embodiment.

First, a user requesting authentication presents the finger 1 to the input device 2. The light source 23 installed in the input device 2 irradiates the finger 1 with infrared light, which is scattered in every direction within the finger 1.

The image pickup device 29 installed in the input device 2 picks up the infrared light exiting the palm side of the finger 1. The image pickup device 29 inputs the image picked up to the authentication processing unit 10 via the image input unit 18.

The authentication processing unit 10 stores the entered image in the memory 12. From the image stored in the memory 12, the authentication processing unit 10 extracts feature data.

The authentication processing unit 10 next obtains, from the storage 14, authentication data stored in advance in the storage 14. The authentication processing unit 10 may retrieve from the storage 14 only authentication data that is associated with information entered from the input unit 16 (e.g., user ID). The obtained authentication information is stored in the memory 12.

The authentication processing unit 10 crosschecks the extracted feature data with the authentication data obtained from the storage 14. To be specific, the authentication processing unit 10 calculates a correlation value between the feature data and the authentication data, to thereby identify a person that has presented the finger 1 to the input device 2.

The authentication processing unit 10 then performs processing suited to the identified person.

The authentication system of this embodiment authenticates users in the manner described above.

Figure 2:
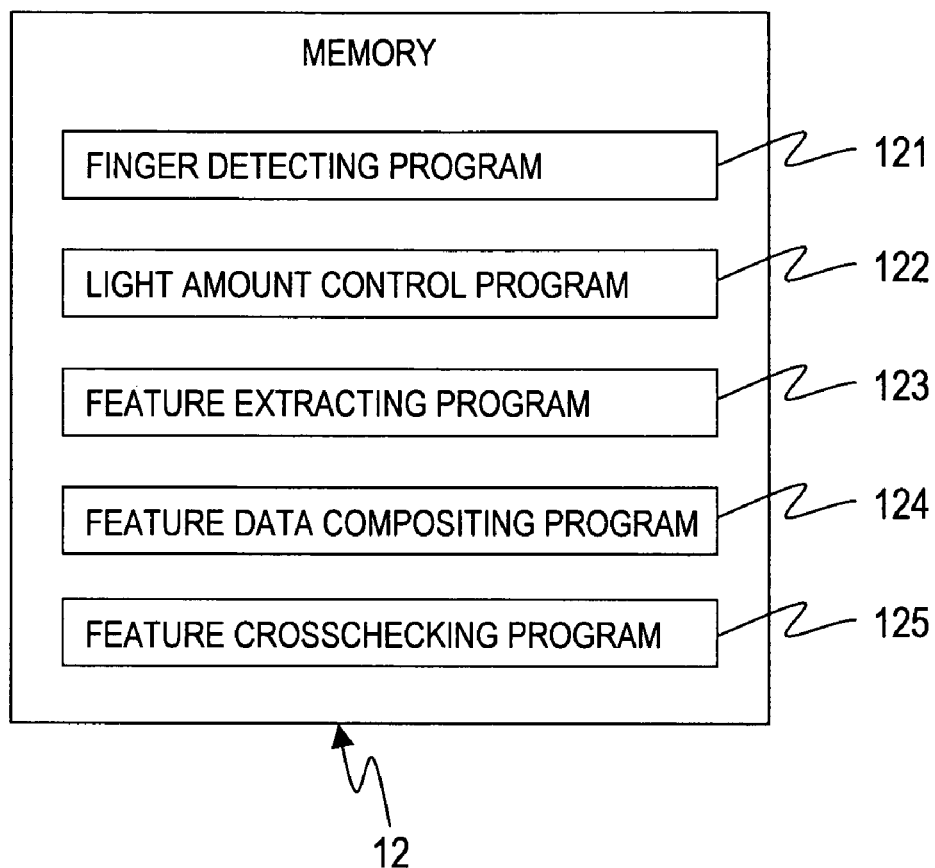
FIG. 2 is a block diagram of a memory in an authentication processing unit according to the first embodiment of this invention.

FIG. 2 is a block diagram of the memory 12 in the authentication processing unit 10 according to the first embodiment of this invention.

The memory 12 stores a finger detecting program 121, a light amount control program 122, a feature extracting program 123, a feature data compositing program 124, a feature crosschecking program 125, and the like.

The finger detecting program 121 judges whether or not the finger 1 is on the input device 2.

The light amount control program 122 controls the intensity of light emitted from the light source 23.

The feature extracting program 123 extracts feature data from an image picked up by the image pickup device 29.

The feature data compositing program 124 pastes together feature data that is extracted by the feature extracting program 123 and feature data that has been extracted in the past.

The feature crosschecking program 125 checks feature data composited by the feature data compositing program 124 against authentication data stored in the storage 14.

Figure 3A:
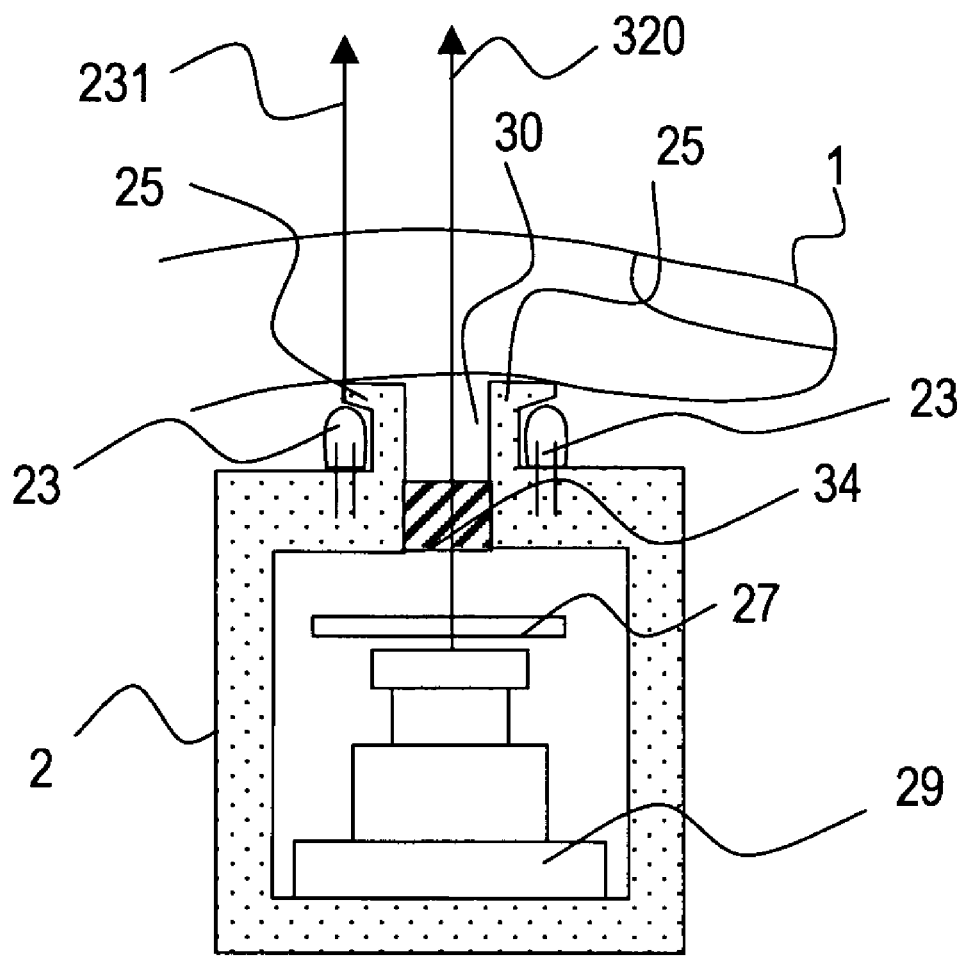
FIG. 3A is a side view of an input device according to the first embodiment of this invention.

FIG. 3A is a side view of the input device 2 according to the first embodiment of this invention. FIG. 3B is a frontal view of the input device 2 according to the first embodiment of this invention. FIG. 3C is a plan view of the input device 2 according to the first embodiment of this invention.

A description on the input device 2 of this embodiment will be given, taking a sweep type finger vein authentication device as an example. A sweep type finger vein authentication device requires a user to move the finger 1 in order to pick up an image of the entire finger 1.

Two finger rests 25 are set on the top of the input device 2 as an interface where a living body whose image is to be picked up is placed. The placement of the two finger rests 25 is such that an opening 30 is provided.

The opening 30 only has to be transmissive of infrared light, and may be an empty space or a member that transmits infrared light. The width of the opening 30 in the longitudinal direction of the finger 1 is smaller than the length of the finger 1 to make the input device 2 small in size.

The finger rests 25 may be integrated with the input device 2, or may be built separately from the input device 2. The finger rests 25 are formed from a material that does not transmit infrared light.

Figure 3B:
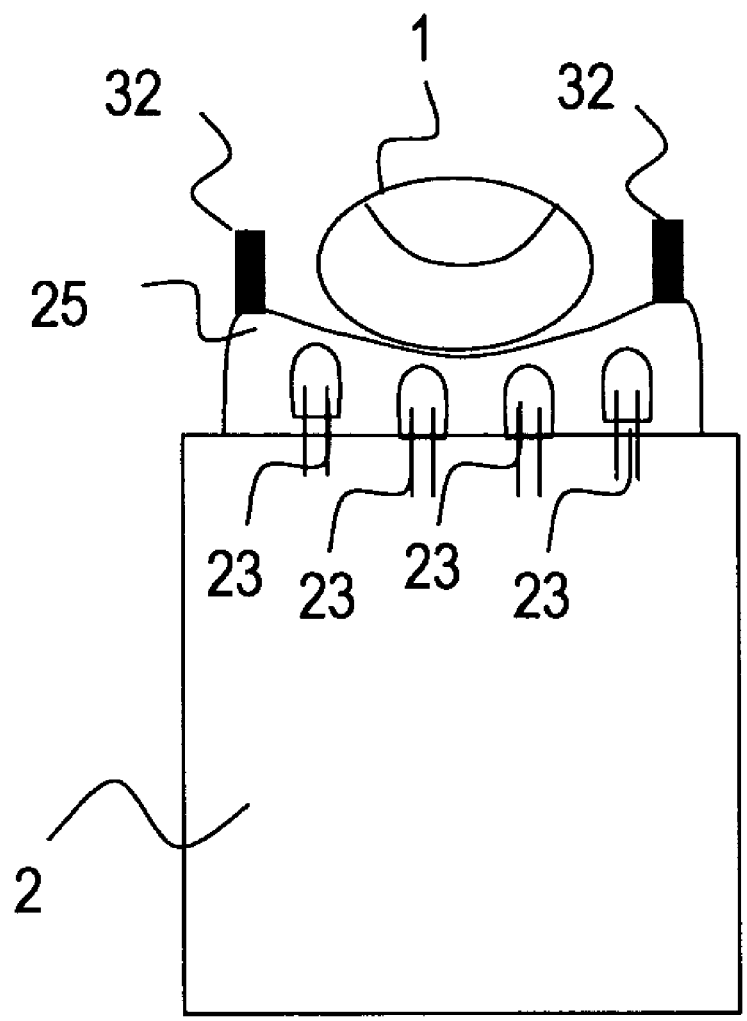
FIG. 3B is a frontal view of the input device according to the first embodiment of this invention.
Figure 3C:
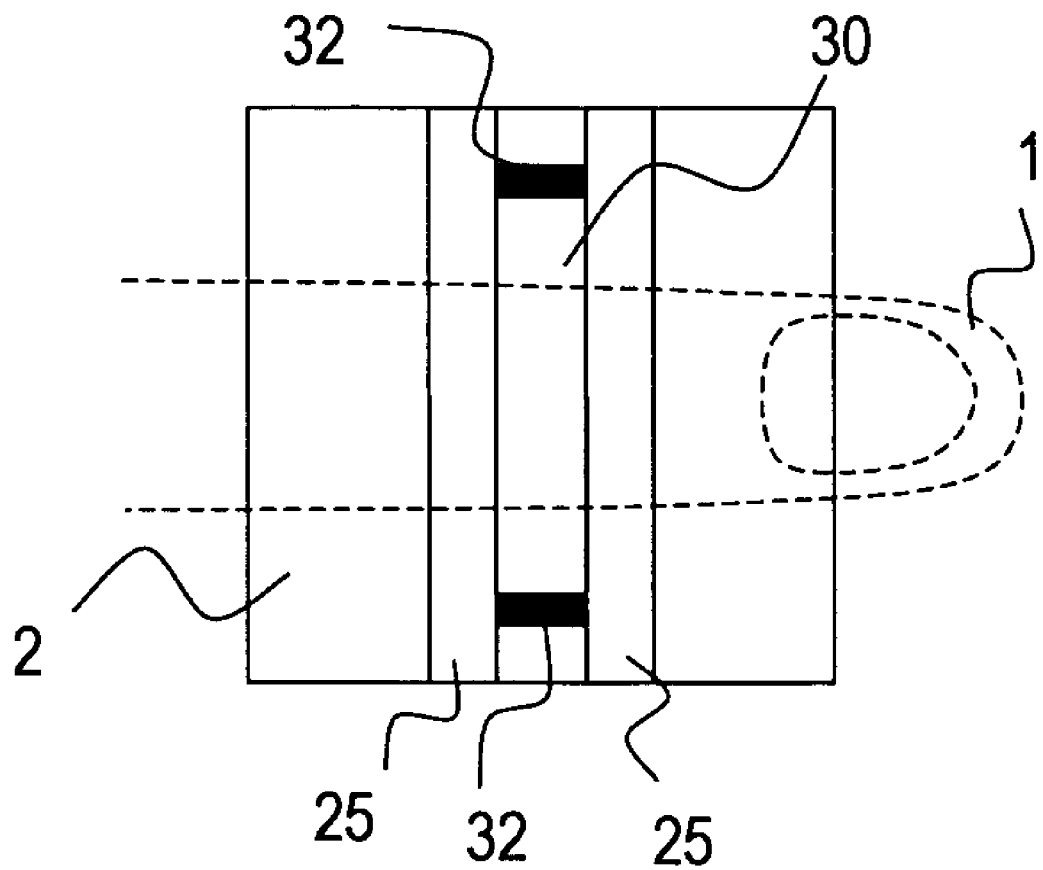
FIG. 3C is a plan view of the input device according to the first embodiment of this invention.

The finger rests 25 have a shape curved to the shape of the finger 1 (see FIG. 3B for example). The finger rests 25 are concave in the center.

This enables a user to place his/her finger at a given position. Furthermore, a user can move the finger 1 stably. The authentication system of this embodiment can thus have an enhanced accuracy of authentication.

The finger rests 25 may have a planar shape instead of a curved, dipped shape. In this case, the finger rests 25 are not concaved or convexed, and accordingly, enables the top of the input device 2 to have a flat-structure. Note that the finger rests 25 are given as an example of an interface to which a finger is presented for authentication, and that the interface can have any shape as long as the interface is placed where the finger 1 is presented for authentication.

Placed under the finger rests 25 is the light source 23. The light source 23 irradiates the finger 1 with infrared light. The light source 23 emits light having an optical axis 231 in a direction substantially parallel to an image pickup direction 320 of the image pickup device 29. The image pickup direction 320 is an optical axis direction in which the image pickup device 29 picks up an image.

In this explanatory diagram, four light sources 23 are placed side by side under each of the finger rests 25 in a direction substantially perpendicular to the longitudinal direction of the finger 1. There can be as many light sources 23 as necessary to irradiate the finger 1 with enough intensity.

On the other hand, lining up plural light sources 23 in a direction substantially perpendicular to the longitudinal direction of the finger 1 makes it possible to irradiate the finger 1 entirely at uniform brightness. It also allows the input device 2 to be narrower in the longitudinal direction of the finger 1. The same effect as when plural light sources 23 are lined up is obtained in a case where one elongated light source 23 is placed in a direction substantially perpendicular to the longitudinal direction of the finger 1.

The CPU 11 of the authentication processing unit 10 controls the intensity of infrared light emitted from the light sources 23 by executing the light amount control program 122. For instance, when a finger joint is put on the finger rests 25, the authentication processing unit 10 lowers the intensity of light, whereas, when a thick portion of the finger 1 is put on the finger rests 25, the authentication processing unit 10 increases the intensity of light.

The authentication processing unit 10 may control the light sources 23 such that all the light sources 23 emit the same amount of light. In this case, the authentication processing unit 10 only needs one stream of electric current to control the light sources 23, and the authentication system can therefore be manufactured at low cost.

The authentication processing unit 10 may also control the light sources 23 such that different light sources 23 emit different amounts of light. In this case, the authentication processing unit 10 uses different streams of electric current to control the light sources 23, and raises the cost of the authentication system. On the other hand, with each light source 23 emitting an adequate amount of light, the image pickup device 29 can pick up a clear image in which a brightness is fluctuated little.

The authentication processing unit 10 may control the light sources 23 such that the light sources 23 set under the finger rest 25 on the root side of the finger 1 and the light sources 23 set under the finger rest 25 on the tip side of the finger 1 emit different amounts of light. In this case, the authentication processing unit 10 needs two streams of electric current to control the light sources 23, and the authentication system can therefore be manufactured at low cost. Furthermore, the image pickup device 29 can pick up a clear image in which the brightness is fluctuated little.

Plural light sources 23 may also be lined up in the longitudinal direction of the finger 1.

Plural light sources 23 may also be arranged in a sheet-shape. In this case, the authentication processing unit 10 controls the light sources 23 such that ones far from the opening 30 emit intense light and ones near the opening 30 emit less intense light. The image pickup device 29 can thus pick up a clear image in which the brightness is fluctuated little.

An acrylic plate 34 is set in the opening 30. The acrylic plate 34 is a material transmissive of infrared light. The acrylic plate 34 prevents a finger and a foreign object including dust from entering the interior of the input device 2.

A light shielding member 32 is set on each side of the top of the opening 30. The light shielding member 32 prevents external light from entering the opening 30. For example, the light shielding member 32 is placed so as to cover each side of the finger 1.

The light shielding member 32 is unnecessary when there is little effect of external light. The light shielding member 32 is also unnecessary when the top of the input device 2 has to have a flat structure.

The image pickup device 29 and an infrared transmitting filter 27 are installed inside the input device 2.

The infrared transmitting filter 27 is set between the acrylic plate 34 and the image pickup device 29. The infrared transmitting filter 27 only transmits infrared light.

The image pickup device 29 picks up infrared light that has entered the input device 2 from the outside and traveled through the opening 30, the acrylic plate 34 and the infrared transmitting filter 27. The image pickup device 29 is placed right under the opening 30. The image pickup device 29 faces upward.

A mirror or the like may additionally be provided in the input device 2. Then, the image pickup device 29 can be set at an arbitrary position and can face an arbitrary direction. This makes it possible to reduce height of the input device 2, for a distance between the opening 30 and the image pickup device 29 can be adjusted by changing the path of infrared light entering from the opening 30 with the mirror or the like.

Alternatively, a planar light receiving device may be installed in the opening 30. The light receiving device detects infrared light. In this case, the acrylic plate 34, the infrared transmitting filter 27 and the image pickup device 29 are omitted, and the input device 2 can thus be made flat.

Processing executed by the input device 2 will be described below.

First, a user requesting authentication puts the finger 1 on the finger rests 25. Then, the light sources 23 irradiate the finger 1 with infrared light, which is scattered in every direction within the finger 1. A part of the infrared light scattered within the finger 1 reaches an area near the top of the opening 30. A part of the infrared light that has reached the area near the top of the opening 30 travels outside of the finger 1.

The infrared light exiting the finger 1 reaches the image pickup device 29 through the opening 30, the acrylic plate 34, and the infrared transmitting filter 27, and is picked up by the image pickup device 29.

The infrared light picked up by the image pickup device 29 has been transmitted from the interior of the finger 1 through a palm side surface of the finger 1. Accordingly, the infrared light picked up by the image pickup device 29 includes a weak component attenuated by being transmitted through finger veins and an intense component which has been transmitted through areas free of finger veins and therefore has not been attenuated. In other words, the infrared light picked up by the image pickup device 29 contains a contrast due to finger veins.

Picking up such infrared light enables the image pickup device 29 to obtain an image of a finger vein pattern in a partial area (i.e., pickup target portion) of the finger 1 that is positioned right above the opening 30.

The opening 30 of the input device 2 according to this embodiment is narrow in the longitudinal direction of the finger 1. The user moves the finger 1 in the longitudinal direction of the finger 1 while keeping the finger 1 on the finger rests 25. At this point, the image pickup device 29 of the input device 2 picks up images of the pickup target portion in succession. The authentication processing unit 10 composites the images picked up by the image pickup device 29, to thereby obtain an image of the whole finger vein pattern of the finger 1.

In order for the image pickup device 29 of the input device 2 to pick up a clear image of a finger vein pattern in the pickup target portion, the following optical conditions are desirably met:

One condition is that the image pickup device 29 does not pick up infrared light that is reflected from the skin surface of the finger 1. Another condition is that the image pickup device 29 does not pick up infrared light that is scattered before reaching a depth where finger veins run.

Unless these optical conditions are met, infrared light that does not carry finger vein pattern information lowers the contrast of the finger vein pattern, and a finger vein pattern image becomes unclear due to unnecessary information such as wrinkles on the skin surface of the finger 1.

To fulfill the optical conditions, the finger rests 25 are set between the light sources 23 and the opening 30, and are formed from a material that does not transmit infrared light.

The light sources 23 emit divergent infrared light (i.e., infrared light with directivity). If formed from a material transmissive of infrared light, the finger rests 25 would let infrared light from the light sources 23 directly reach the pickup target portion above the opening 30. Then, the infrared light that has directly reached the pickup target portion is reflected from the skin surface of the pickup target portion and then reaches the image pickup device 29, thus failing to fulfill the optical conditions. The finger rests 25 therefore have to be formed from a material that does not transmit infrared light.

Desirably, materials that do not reflect infrared light are used for inner walls of the input device 2, the filter 27, the image pickup device 29 and the acrylic plate 34. This is to prevent infrared light that exits the finger 1 from being reflected within the input device 2 and traveling back to the surface of the finger 1.

Further, the finger rests 25 also cover more than half of the upper portions of the light sources 23 on the side of the opening 30 in order to fulfill the optical conditions. This enables the image pickup device 29 to pick up an image of a finger vein pattern while hardly being affected by infrared light that is scattered without reaching a depth where finger veins run (for example, infrared light that is scattered near the surface of the finger 1).

How it is so will be described below.

Figure 4A:
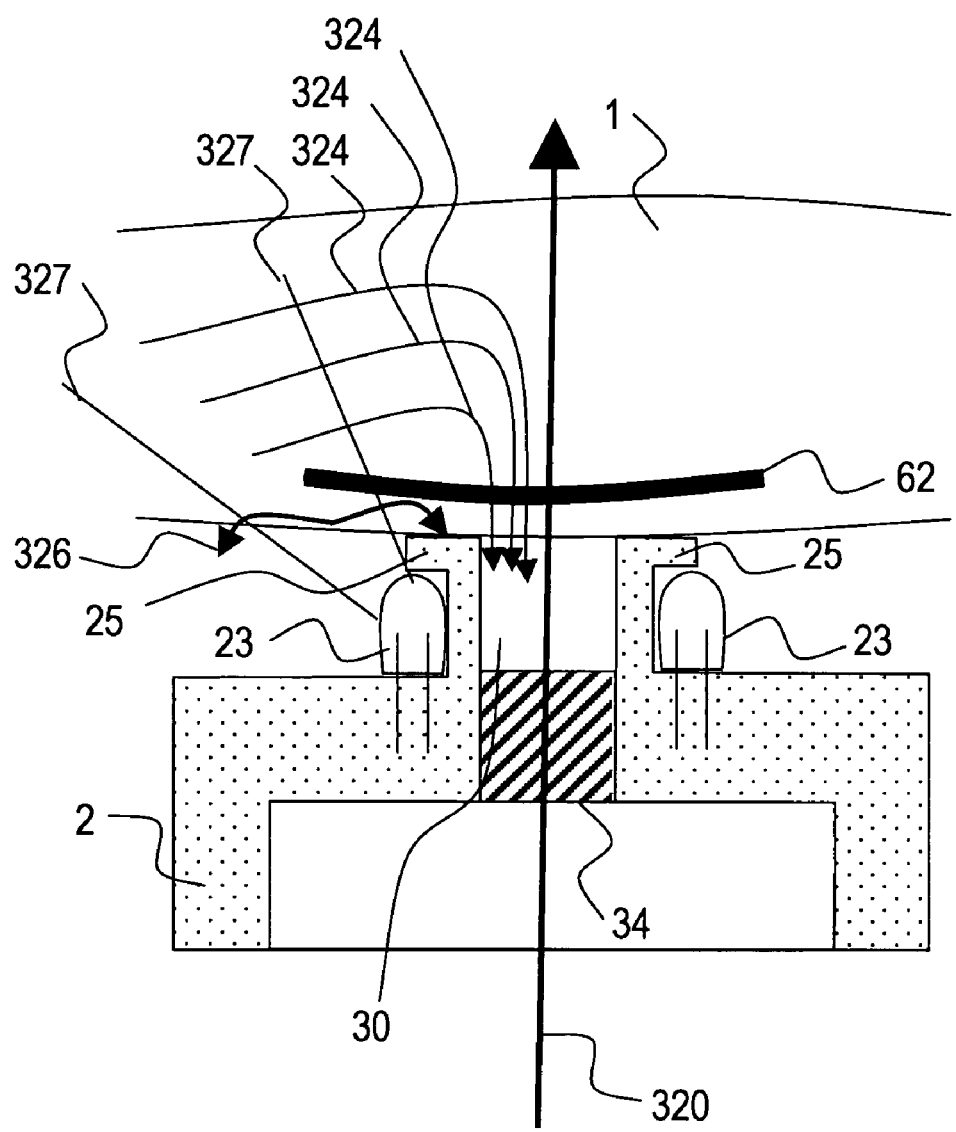
FIG. 4A is an explanatory diagram showing effects of a shape of a finger rest according to the first embodiment of this invention.

FIG. 4A is an explanatory diagram showing effects of the shape of the finger rests 25 according to the first embodiment of this invention.

In this explanatory diagram, the finger rests 25 cover more than half of the upper portions of the light sources 23 on the opening 30 side. Therefore, infrared light emitted from each light source 23 is directed toward a direction opposite to the opening 30.

The finger rests 25 are placed such that the divergence of infrared light from the light sources 23 does not include the image pickup direction 320. In other words, the finger rests 25 are set such that every component of infrared light from the light sources 23 travels toward a direction opposite to the opening 30. The divergence of infrared light emitted from the light sources 23 is of a range between border lines 322. The image pickup direction 320 is an optical axis direction in which the image pickup device 29 picks up an image.

In this embodiment, the light sources 23 emit light with an optical axis in a direction substantially parallel to the image pickup direction 320.

A path infrared light takes in this case will be described next.

Infrared light from the light sources 23 first reaches the finger 1. A part of the infrared light that has reached the finger 1 is reflected from the skin surface of the finger 1 whereas another part of the same infrared light enters into the finger 1.

The infrared light that is reflected from the skin surface of the finger 1 is shielded by the finger rests 25 and does not reach the top of the opening 30.

Infrared light 326, which is a part of the infrared light that has entered into the finger 1, is scattered without reaching a depth where finger veins 62 run, whereas infrared light 324, which is a part of the infrared light that has entered into the finger 1, is scattered after reaching the depth where the finger veins 62 run.

The infrared light 326 that is scattered before reaching the depth where the finger veins 62 run changes its travel direction. However, very little of the infrared light 326 reaches the top of the opening 30 since most components of infrared light that has entered the finger 1 travel in a direction opposite to the opening 30.

The infrared light 324, which is scattered after reaching the depth where the finger veins 62 run, is partially absorbed by the finger veins 62. Another part of the infrared light 324 reaches the top of the opening 30. The infrared light 324 thus reaches the top of the opening 30 while carrying finger vein pattern information.

By picking up this infrared light 324, the image pickup device 29 can thus pick up a finger vein pattern image. The finger vein pattern image picked up by the image pickup device 29 is affected very little by the infrared light 326, which is scattered before reaching the depth where the finger veins 62 run and the infrared light that is reflected from the skin surface of the finger 1.

Figure 4B:
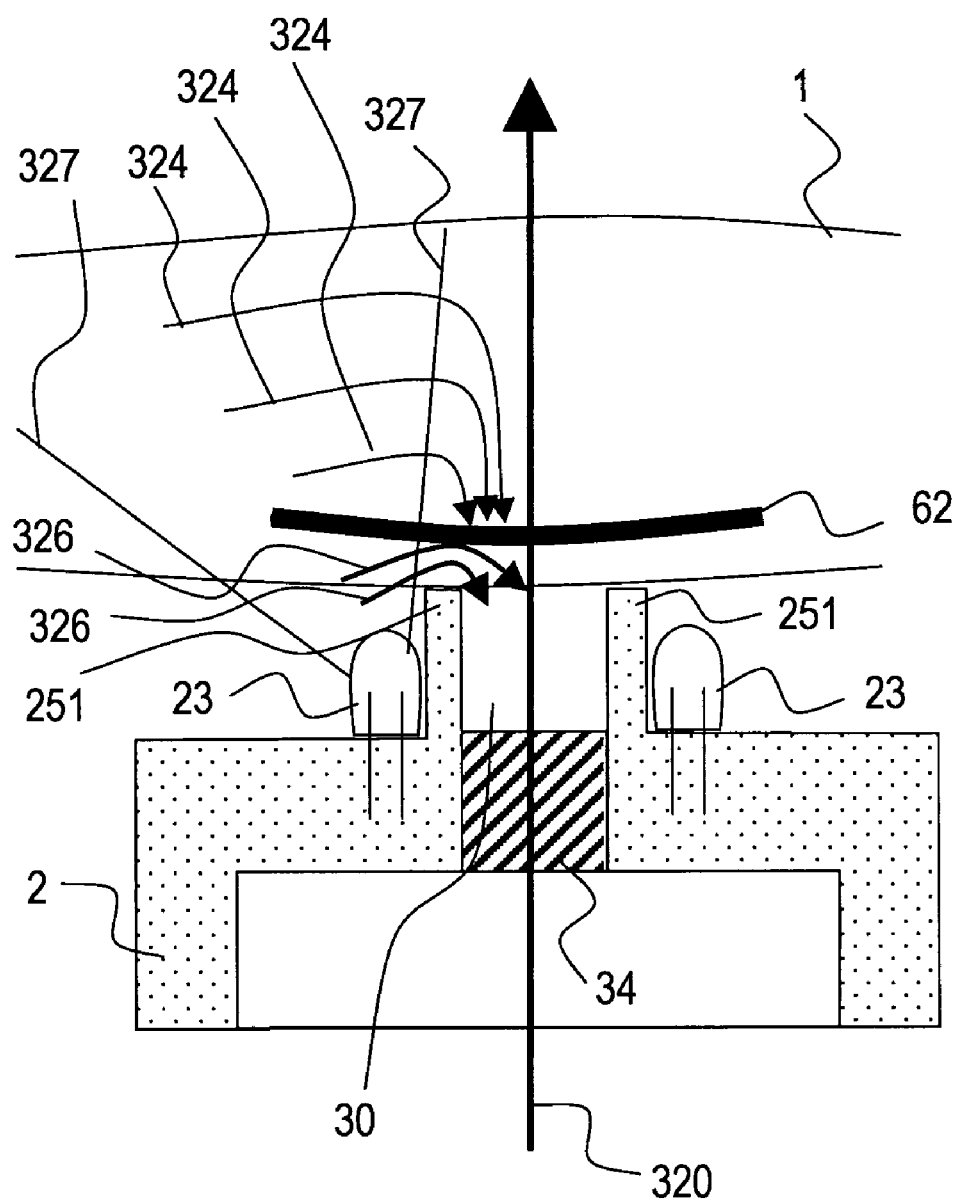
FIG. 4B is an explanatory diagram showing effects of the shape of the finger rest according to the first embodiment of this invention.

FIG. 4B is an explanatory diagram showing effects of the shape of the finger rests 25 according to the first embodiment of this invention.

In this explanatory diagram, the finger rests 251 do not have light shielding portions over the light sources 23 unlike the finger rests 25 of this embodiment. For comparison with the finger rests 25 of this embodiment, a path infrared light takes when finger rests 251 are employed will be described.

The divergence of infrared light emitted from the light sources 23 is, in this case, of a range between border lines 327, and includes the image pickup direction 320. In other words, the infrared light from the light sources 23 contains components directed toward the opening 30.

A path the infrared light takes is described next.

The infrared light takes the same path as when the finger rests 25 are employed (FIG. 4A) except for the path of the infrared light 326, which is scattered before reaching the depth where the finger veins 62 run. A description on the common infrared light path will be omitted.

The infrared light from the light sources 23 in this explanatory diagram contains components directed toward the opening 30. A part of the infrared light 326 scattered before reaching the depth where the finger veins 62 run therefore reaches the top of the opening 30.

In short, with the finger rests 251 not covering the upper portions of the light sources 23, the image pickup device 29 picks up a finger vein pattern image that is affected by the infrared light 326, which is scattered before reaching the depth where the finger veins 62 run. The image pickup device 29 thus cannot pick up a clear image of a finger vein pattern.

In contrast, with the finger rests 25 covering more than half of the upper portions of the light sources 23 on the opening 30 side, the image pickup device 29 can pick up a clear finger vein pattern image which is hardly affected by the infrared light 326, which is scattered before reaching the depth where the finger veins 62 run.

Since the input device 2 of this embodiment is a sweep type authentication device, a user moves the finger 1 in the longitudinal direction of the finger 1 while keeping the finger 1 on the finger rests 25. It can be expected that the user may accidentally lift the finger 1 from the finger rests 25 while moving the finger 1. In this case, too, the finger rests 25 covering more than half of the upper portions of the light sources 23 on the opening 30 side enable the image pickup device 29 to pick up a clear finger vein pattern image.

A mechanism thereof will be described below.

Figure 5A:
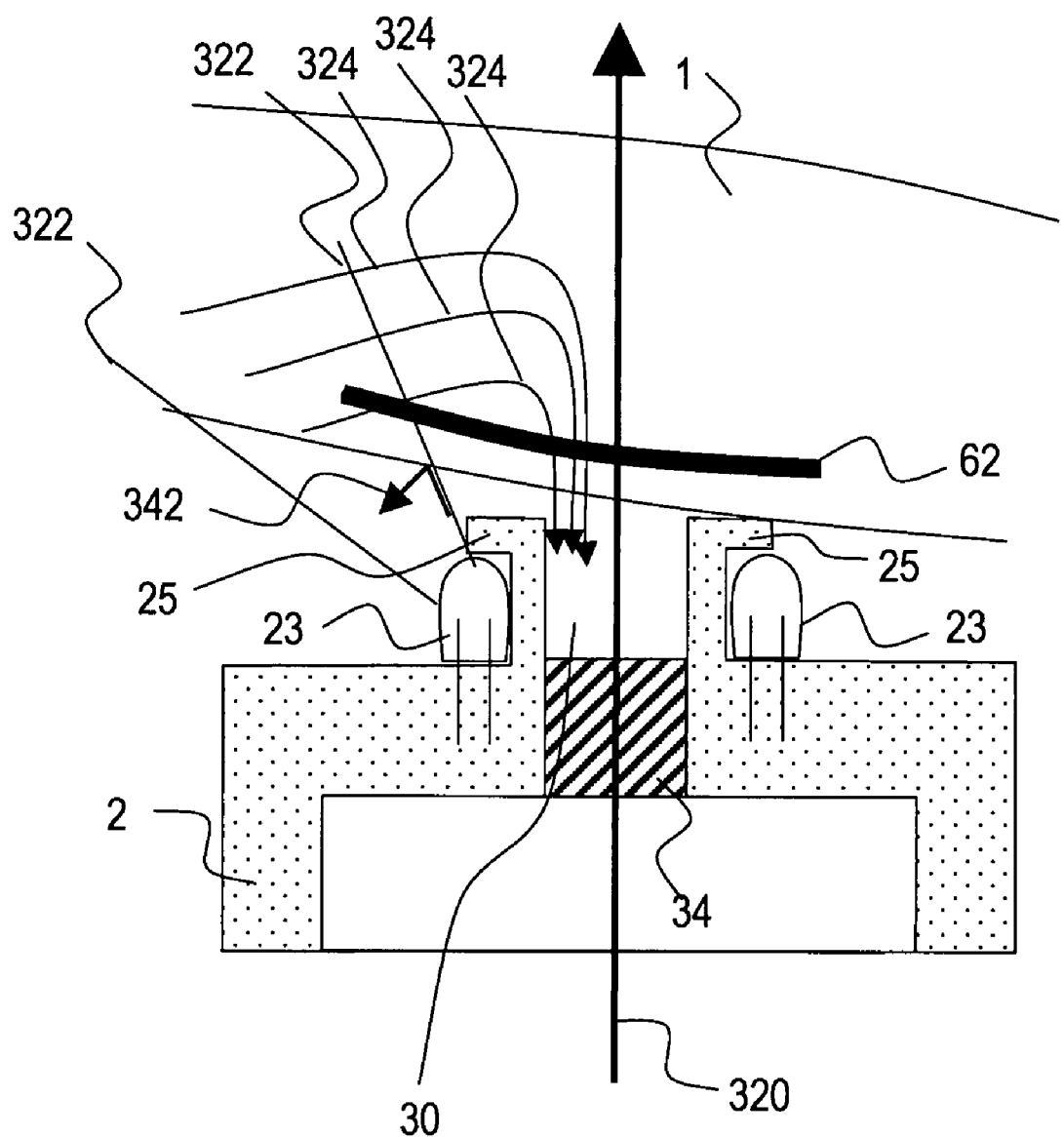
FIG. 5A is an explanatory diagram showing effects of the shape of the finger rest according to the first embodiment of this invention.

FIG. 5A is an explanatory diagram showing effects of the shape of the finger rests 25 according to the first embodiment of this invention.

In this explanatory diagram, the finger rests 25 cover more than half of the upper portions of the light sources 23 on the opening 30 side, and thus direct infrared light emitted from the light sources 23 toward a direction opposite to the opening 30.

The finger rests 25 are placed such that the divergence of infrared light from the light sources 23 does not include the image pickup direction 320. In other words, the finger rests 25 are set such that every component of infrared light from the light sources 23 travels toward a direction opposite to the opening 30. The divergence of infrared light emitted from the light sources 23 is of a range between the border lines 322. The image pickup direction 320 is an optical axis direction in which the image pickup device 29 picks up an image.

A path infrared light takes in this case is described next.

Infrared light from the light sources 23 first reaches the finger 1. Infrared light 342, which is a part of the infrared light that has reached the finger 1, is reflected from the skin surface of the finger 1 whereas the infrared light 324, which is another part of the same infrared light, enters into the finger 1.

The infrared light 324, which has entered into the finger 1, takes the same path as in FIG. 4A, and a description of the path will be omitted.

On the other hand, the infrared light 342 reflected from the surface of the finger 1 changes its travel direction. However, very little of the infrared light 342 reaches the top of the opening 30 since the infrared light that reaches the finger 1 is directed toward a direction opposite to the opening 30. In other words, most components of the infrared light 342 reflected from the surface of the finger 1 travel in a direction opposite to the opening 30.

Figure 5B:
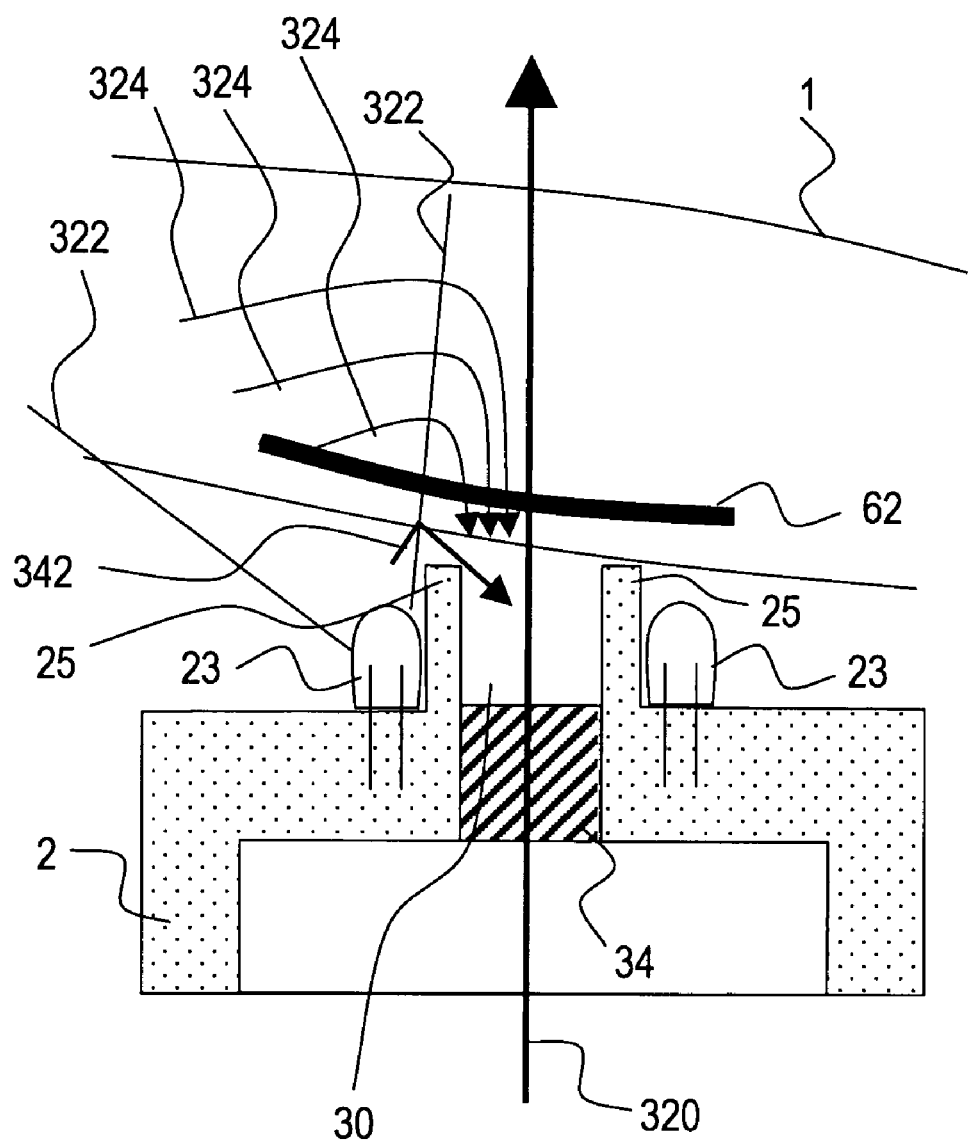
FIG. 5B is an explanatory diagram showing effects of the shape of the finger rest according to the first embodiment of this invention.

FIG. 5B is an explanatory diagram showing effects of the shape of the finger rests 25 according to the first embodiment of this invention.

In this explanatory diagram, the finger rests 251 do not have light shielding portions over the light sources 23 unlike the finger rests 25 of this embodiment. For comparison with the finger rests 25 of this embodiment, a path infrared light takes when the finger rests 251 are employed will be described.

The divergence of infrared light emitted from the light sources 23 is, in this case, of a range between the border lines 327, and includes the image pickup direction 320. In other words, the infrared light from the light sources 23 contains components directed toward the opening 30.

A path the infrared light takes is described next.

The infrared light takes the same path as when the finger rests 25 are employed (FIG. 5A) except for the path of the infrared light 342, which is reflected from the surface of the finger 1. A description on the common infrared light path will be omitted.

The infrared light from the light sources 23 in this explanatory diagram contains components directed toward the opening 30. A part of the infrared light 342 reflected from the surface of the finger 1 therefore reaches the top of the opening 30.

In short, with the finger rests 251 not covering the upper portions of the light sources 23, the image pickup device 29 picks up a finger vein pattern image that is affected by the infrared light 342, which is reflected from the surface of the finger 1. The image pickup device 29 thus cannot pick up a clear image of a finger vein pattern.

In contrast, with the finger rests 25 covering more than half of the upper portions of the light sources 23 on the opening 30 side, the image pickup device 29 can pick up a clear finger vein pattern image which is hardly affected by the infrared light 342 reflected from the surface of the finger 1.

The finger rests 25 therefore have to cover the upper portions of the light sources 23 in order to keep the divergence of infrared light emitted by the light sources 23 away from the opening 30.

The finger rests 25 may be made wide enough, so that the upper portions of the light sources 23 do not need to be covered. In this case, the input device 2 is made large in size, but the image pickup device 29 is able to pick up a finger vein pattern image that is affected very little by the infrared light 326, which is scattered before reaching the depth where the finger veins 62 run, and the infrared light, which is reflected from the skin surface of the finger 1.

Described next is a finger vein pattern image picked up by the image pickup device 29.

Figure 6:
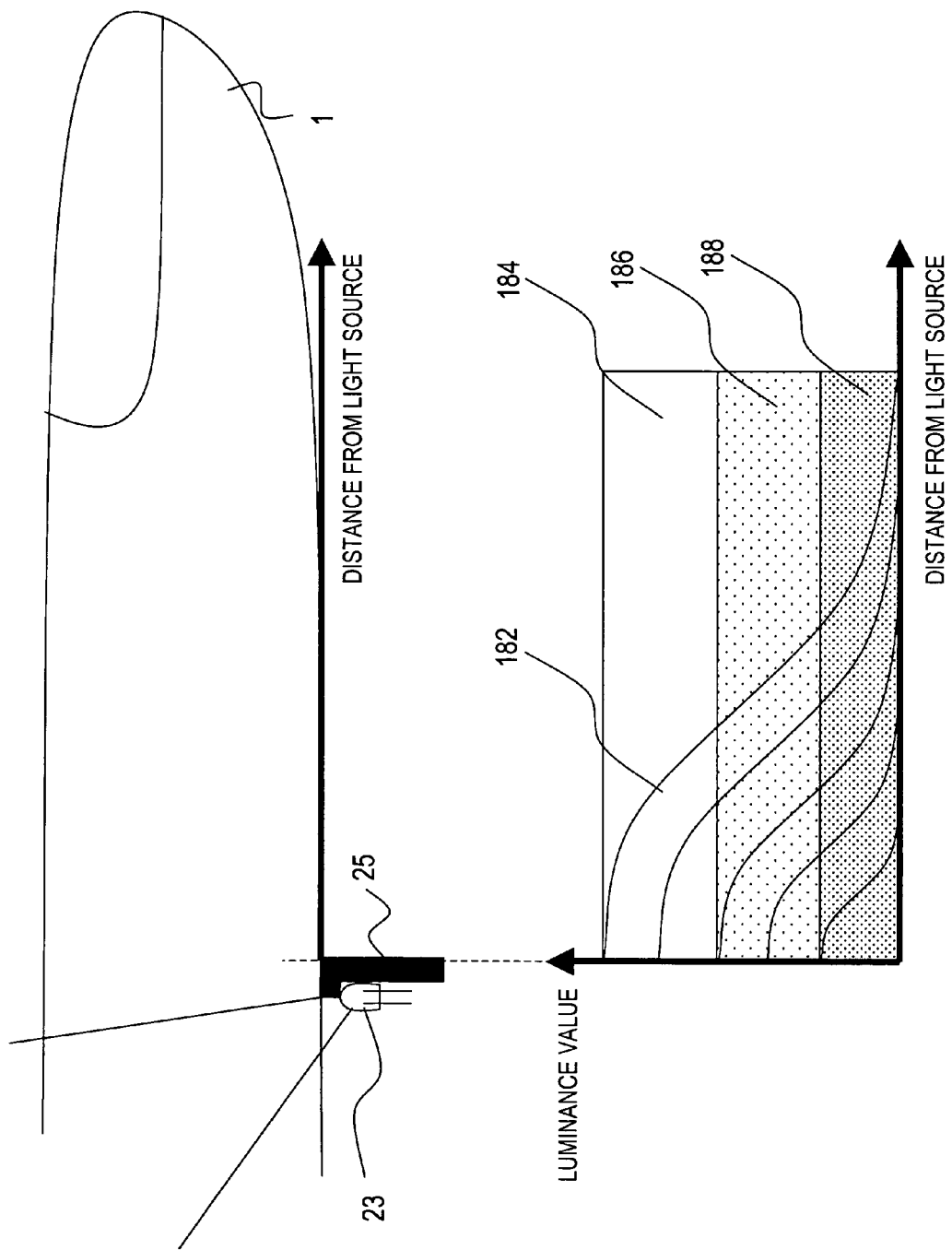
FIG. 6 is an explanatory diagram showing a relation between a distance from a light source and a luminance value of a finger vein pattern image according to the first embodiment of this invention.

FIG. 6 is an explanatory diagram showing a relation between the distance from the light source 23 and the luminance value of a finger vein pattern image according to the first embodiment of this invention.

A graph in FIG. 6 shows a relation between the distance from the light source 23 and the luminance value of a finger vein pattern image.

A case in which the light source 23 emits infrared light at a fixed intensity will be described first.

The luminance value of the image is high when the distance from the light source 23 is short. As the distance from the light source 23 increases, the luminance value of the image is lowered. Increasing the distance from the light source 23 causes the luminance value of the image to drop rapidly when a luminance measurement point is near the light source 23. On the other hand, increasing the distance from the light source 23 causes the luminance value of the image to drop slowly when a luminance measurement point is far from the light source 23.

A luminance value is classified into a high luminance range 184, a visible range 186 and a low luminance range 188.

When an image has a luminance value in the high luminance range 184, the authentication processing unit 10 cannot obtain finger vein pattern information from the image since this image is saturated with light.

When an image has a luminance value in the visible range 186, the authentication processing unit 10 can obtain finger vein pattern information from the image.

When an image has a luminance value in the low luminance range 188, the authentication processing unit 10 cannot obtain finger vein pattern information from the image since light in this image is too weak.

In short, the visible range 186 is a range in which the image pickup device 29 can detect variation in light intensity, whereas the high luminance range 184 and the low luminance range 188 are ranges in which the image pickup device 29 cannot detect variation in light intensity.

A curve representing the luminance value of the image moves toward the upper right corner of the graph when the intensity of infrared light emitted from the light source 23 is increased. In other words, increasing the light amount of the light source 23 moves the visible range 186 away from the light source 23.

The curve representing the luminance value of the image moves toward the lower left corner of the graph when the intensity of infrared light emitted from the light source 23 is reduced. In other words, lowering the light amount of the light source 23 moves the visible range 186 nearer to the light source 23.

This explanatory diagram shows the luminance value given to the image by the light source 23 that is on the root side of the finger 1. The luminance value given to the image by the fingertip side light source 23 is represented by a curve that is a mirror reverse of the curve of FIG. 6.

The luminance value given to the image by the light source 23 on the root side of the finger 1 and the fingertip side light source 23 is represented by a curve that is obtained by overlapping the above two curves.

In this embodiment, where the opening 30 is sufficiently narrower than the visible range 186, the entire area of the opening 30 can be contained in the visible range 186 by adjusting the intensity of infrared light emitted from the light sources 23.

The light sources 23 may be set on either the root side or tip side of the finger 1 instead of on both sides. In this case, also, the entire area of the opening 30 can be contained in the visible range 186 since the opening 30 is sufficiently narrower than the visible range 186. A side where no light sources 23 are set may have or may not have the finger rest 25.

However, setting the finger rest 25 on the side that has no light sources 23 helps to prevent the finger 1 from straying while moving. On the other hand, omitting the finger rest 25 and the light sources 23 on the root side of the finger 1 or on the tip side of the finger 1 enables the input device 2 to have an even smaller size.

In a case where it is not possible to contain the width of the opening 30 in the visible range 186, the intensity of light emitted from the light source 23 is changed in a continuous manner, and the image pickup device 29 picks up an image at each intensity of light. The authentication processing unit 10 composites the images thus picked up by the image pickup device 29, to thereby obtain a whole image of the opening 30 widthwise.

FIG. 7 is a flow chart for authentication processing of the authentication processing unit 10 according to the first embodiment of this invention.

The authentication processing unit 10 first performs finger detection processing (S100) to judge whether or not the finger 1 is on the finger rests 25 (S110).

Whether the finger 1 is on the finger rests 25 or not is judged from information provided by, for example, a contact sensor, a temperature sensor, an electric resistance sensor, or a dielectric sensor. An image picked up by the image pickup device 29 may also be used to judge whether the finger 1 is on the finger rests 25 or not.

A specific description will be given on a case of using an image picked up by the image pickup device 29. This case requires no sensor and the authentication system can accordingly be built at low cost.

The light sources 23 in this case are lit in a regular cycle. The image pickup device 29 picks up an image in a cycle shorter than the lighting cycle of the light sources 23. The image pickup device 29 sends the images picked up to the authentication processing unit 10.

The authentication processing unit 10 receives the images from the image pickup device 29 and obtains the luminance values of the received images. Then, the authentication processing unit 10 compares the luminance values of the images received in succession, to thereby obtain the amount of image luminance value fluctuation. Based on the obtained image luminance value fluctuation amount, the authentication processing unit 10 judges whether or not the finger 1 is on the finger rests 25.

To be specific, the authentication processing unit 10 judges that the finger 1 is not on the finger rests 25 when the image luminance value fluctuation amount is smaller than a threshold. This is because infrared light emitted from the light sources 23 does not reach the image pickup device 29 unless the finger 1 is on the finger rests 25.

When the image luminance value fluctuation amount is equal to or larger than the threshold, it is judged that the finger 1 is on the finger rests 25, because, with the finger 1 resting on the finger rests 25, infrared light emitted from the light sources 23 is scattered inside the finger 1 and reaches the image pickup device 29.

In the case where it is judged that the finger 1 is not on the finger rests 25, authentication processing is not necessary and the authentication processing unit 10 returns to Step S100.

On the other hand, in the case where it is judged that the finger 1 is on the finger rests 25, the authentication processing unit 10 performs light amount control processing (S120).

To be specific, the light amount of the light sources 23 is controlled such that the luminance value of an image picked up by the image pickup device 29 approaches an objective value. The objective value is a luminance value that yields maximum contrast between a vein portion and a non-vein tissue portion. The objective value is constant regardless of the shape and thickness of the finger 1.

Described here is a case in which the authentication processing unit 10 controls the fingertip side light sources 23 and the light sources 23 on the root side of the finger 1 separately.

The authentication processing unit 10 receives images from the image pickup device 29. The authentication processing unit 10 calculates a mean luminance value in the fingertip side halves of the received images and a mean luminance value in the finger root side halves of the same images.

The light amount of the light sources 23 is controlled in accordance with the obtained mean luminance values. To be specific, the light amount of the fingertip side light sources 23 is controlled such that the mean luminance value in the fingertip side halves approaches the objective value, and the light amount of the light sources 23 on the root side of the finger 1 is controlled such that the mean luminance value in the finger root side halves approaches the objective value.

The authentication processing unit 10 makes the image luminance values closer to the objective value by increasing or reducing the light amount of the light sources 23 while feeding back the image luminance values. The light amount of the light sources 23 may be increased or reduced by a fixed amount, or by an amount varied in accordance with the degree of convergence. Alternatively, the authentication processing unit 10 may estimate, based on characteristics of the image pickup device 29, a light amount that will make the image luminance values closer to the objective value, and then have the light sources 23 emit the estimated amount of light.

The authentication processing unit 10 next performs feature extracting processing (S130). The feature extracting processing is, as will be described later with reference to FIGS. 8A, 8 and 8C, for extracting feature data from the images picked up by the image pickup device 29.

Next, performed is feature data compositing processing (S140). The feature data compositing processing is, as will be described later with reference to FIG. 9, for pasting together the extracted feature data and feature data that has been extracted in the past.

The authentication processing unit 10 next judges whether or not the size of the composited feature data is equal to or larger than a threshold (S150). The threshold is determined by a size feature data needs to have for a crosscheck.

To be specific, the movement amount of the finger 1 is calculated through the feature data compositing processing (S140). From the obtained movement amount of the finger 1, the authentication processing unit 10 judges whether or not the size of the feature data is equal to or larger than the threshold.

When the feature data size is smaller than the threshold, the authentication processing unit 10 cannot perform the feature crosschecking processing. Then, the authentication processing unit 10 returns to Step S120.

When the feature data size is equal to or larger than the threshold, the feature crosschecking processing (S160) is performed.

In Step S150, whether or not the movement speed of the finger 1 has become slower than a threshold may be judged additionally. In this case, the feature crosschecking processing (S160) is performed when the feature data size is equal to or larger than the threshold and at the same time the movement speed of the finger 1 is slower than the threshold.

The movement amount of the finger 1 varies depending on the finger length. Therefore, in some cases, there may still be room for the finger 1 to move further after the feature data size exceeds the threshold. In this case, feature data is kept collected until the finger 1 stops moving or until immediately before the finger 1 stops moving. At a point when feature data is collected to the maximum size, the feature crosschecking processing (S160) is started. In this way, the recognition rate can be enhanced even more.

To be specific, the feature data composited in Step S140 is checked against authentication data stored in the storage 14.

For instance, the similarity between the feature data and the authentication data is calculated, and when the obtained similarity is equal to or larger than a threshold, the user is authenticated as a person associated with the authentication data.

This completes the authentication processing.

There is a possibility that the feature data composited in the feature data compositing processing (S140) is distorted. The authentication processing unit 10 deals with the possibility by employing a crosschecking method that takes distortion into account in the feature crosschecking processing (S160).

Examples of the crosschecking method that takes distortion into account include one in which images are enlarged or reduced for a crosscheck, and one in which each image is divided into sections to check corresponding sections against each other and make a comprehensive judgment from the individual crosscheck results. In the method where images are enlarged or reduced for a crosscheck, a distortion in the movement direction of the finger 1 is adjusted appropriately by raising the expansion/contraction rate in the longitudinal direction of the finger 1.

The feature extracting processing (S130) of the authentication processing unit 10 will be described below.

Figure 8A:
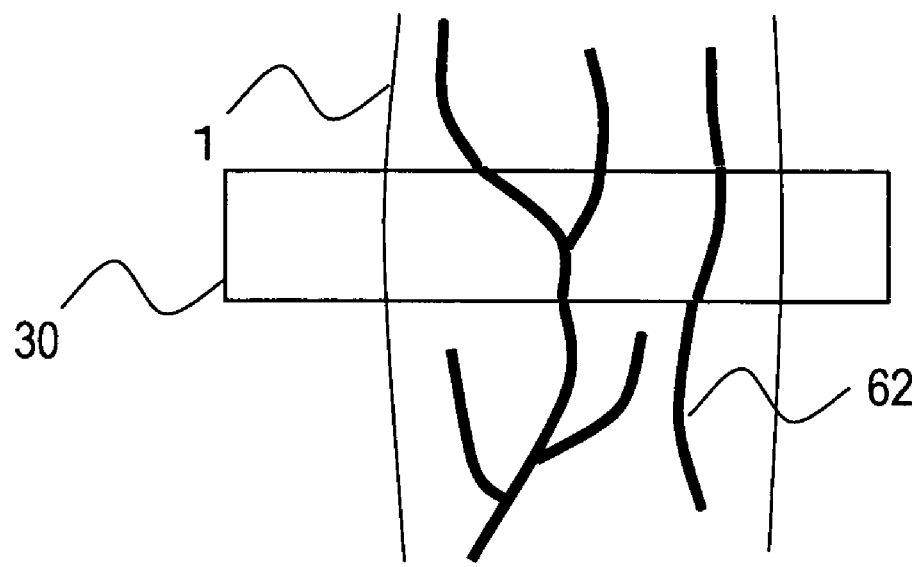
FIG. 8A is an explanatory diagram of finger veins whose image is picked up by an image pickup device according to the first embodiment of this invention.

FIG. 8A is an explanatory diagram of the finger veins 62 whose image is picked up by the image pickup device 29 according to the first embodiment of this invention.

The finger veins 62 run all over the finger 1 whereas the image pickup device 29 picks up an image of the finger 1 presented to the opening 30, which means that the image pickup device 29 picks up an image of a part of the finger veins 62 that is within an area framed by the opening 30.

Figure 8B:
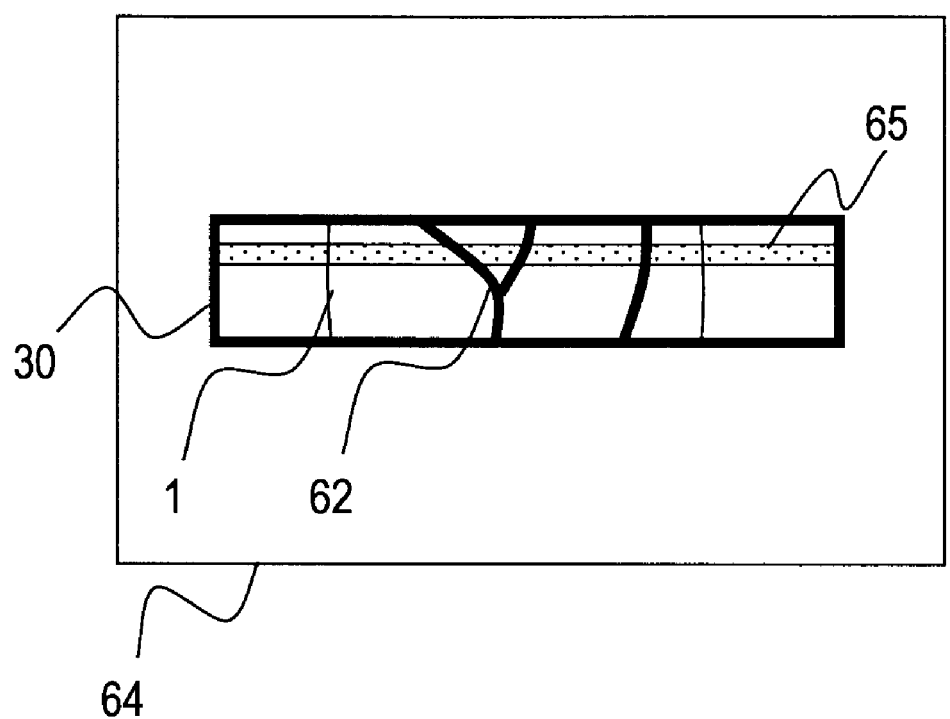
FIG. 8B is an explanatory diagram of an image picked up by the image pickup device according to the first embodiment of this invention.

FIG. 8B is an explanatory diagram of an image 64, which is picked up by the image pickup device 29 according to the first embodiment of this invention.

The image 64 is an image picked up by the image pickup device 29. The image 64 shows a part of the finger 1 and a part of the finger veins 62 that are within an area framed by the opening 30.

The authentication processing unit 10 extracts an area that is framed by the opening 30 from the image 64 picked up by the image pickup device 29.

The area framed by the opening 30 may be set in advance or may be determined automatically by the authentication processing unit 10.

Described here is a method in which the authentication processing unit 10 automatically determines the area framed by the opening 30.

The authentication processing unit 10 judges the area framed by the opening 30 based on luminance differences in an image picked up by the image pickup device 29. The image has to be picked up while the light sources 23 are emitting light and the finger 1 is resting on the finger rests 25.

The authentication processing unit 10 next extracts a finger vein pattern image from the image area cut out as the area framed by the opening 30.

To be specific, a finger vein pattern image is extracted with the use of a common image processing method. Examples of the common image processing method include dark line tracing, linear pattern enhancement through filtering processing, and linear pattern extraction based on the curvature of an image luminance profile curve.

The authentication processing unit 10 may extract a finger vein pattern image after performing finger outline detecting processing on the image area cut out as the area framed by the opening 30. In the finger outline detecting processing, a finger area is discriminated from the rest to detect the outline of the finger 1. The authentication processing unit 10 can extract a finger vein pattern image with high precision by performing the finger outline detecting processing prior to the extraction.

To be specific, the outline of the finger 1 is detected with the use of a common image processing method. Examples of the common image processing method include edge enhancing processing and outline tracing processing.

For instance, the authentication processing unit 10 controls the light sources 23 such that the light sources 23 blink on and off. At this time, the image pickup device 29 picks up images when the light sources 23 are on and when the light sources 23 are off, respectively, and enters both of the images into the authentication processing unit 10.

The authentication processing unit 10 obtains the respective luminance values of the entered images (the image picked up when the light sources 23 are on and the image picked up when the light sources 23 are off. The authentication processing unit 10 detects, as a finger area, an area in which the image has a large difference in luminance value between when the light sources 23 are on and when the light sources 23 are off. The authentication processing unit 10 can thus detect the outline of the finger 1 stably by comparing the image of when the light sources 23 are on and the image of when the light sources 23 are off.

The following method may also be employed to detect the outline of the finger 1:

The image pickup device 29 picks up an image when the light sources 23 on one side of the finger 1 emit intense light and the light sources 23 on the other side of the finger 1 emit weak light. The image pickup device 29 next picks up an image when the intense light side and the weak light side are switched. The image pickup device 29 enters the images picked up to the authentication processing unit 10.

The authentication processing unit 10 detects, as a finger area, an area in which a difference in luminance value is large between the images entered.

The authentication processing unit 10 converts the extracted finger vein pattern image into feature data.

Figure 8C:
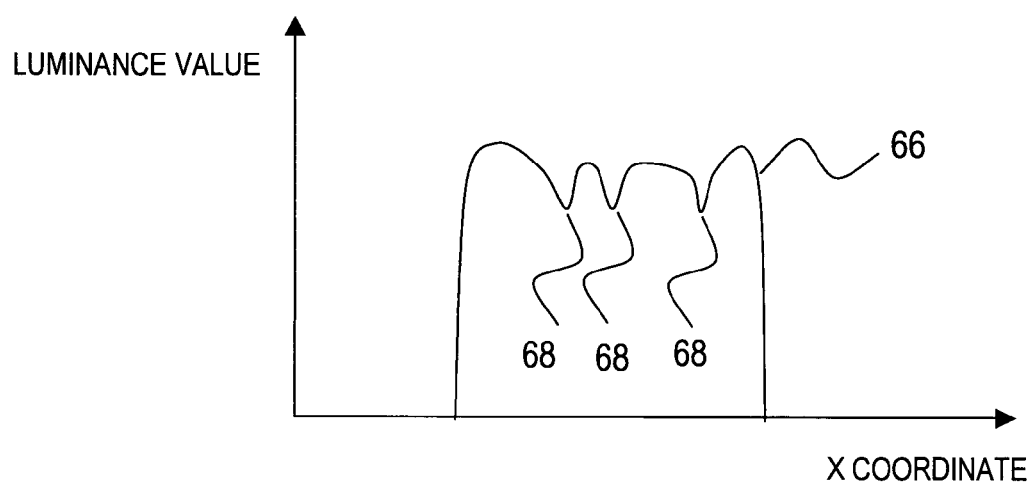
FIG. 8C is an explanatory diagram of feature data converted by the authentication processing unit according to the first embodiment of this invention.

FIG. 8C is an explanatory diagram of feature data 66, which is obtained through conversion executed by the authentication processing unit 10 according to the first embodiment of this invention.

The feature data 66 is information checked against cross-check data which is stored in the storage 14.

The feature data 66 shows the association between a position in an image (an x coordinate) and a luminance value. The x axis is in a direction substantially perpendicular to the longitudinal direction of the finger 1. The feature data 66 of this explanatory diagram is about an area 65 in the image 64 (FIG. 8B).

The feature data 66 has plural local minimum points 68. The local minimum points 68 represent finger vein positions since blood in finger veins absorbs infrared light emitted from the light sources 23.

Feature data may be a finger vein pattern image used in template matching, or may be line segment structural information. Line segment structural information is abstract information on finger veins which contains information about branching points and end points of finger veins.

Described below is the feature data compositing processing (S140) of the authentication processing unit 10.

FIG. 9 is an explanatory diagram of the feature data compositing processing (S140), which is executed by the authentication processing unit 10 according to the first embodiment of this invention.

This explanatory diagram takes as an example a case in which feature data is a finger vein pattern image that is used in template matching. The processing is executed in a similar way even when feature data is other information including, e.g., line segment structural information.

The authentication processing unit 10 composites the feature data extracted through the feature extracting processing (S130). Described here is a case in which the authentication processing unit 10 pastes feature data 80, which is extracted from the frame N image 64, to feature data 82, which is extracted from frame 1 to frame N−1 images. Frame N indicates the order in which images are picked up by the image pickup device 29. An image of the finger 1 that is picked up first by the image pickup device 29 is a frame 1 image.

First, the authentication processing unit 10 moves the position of the feature data 80 extracted from the frame N image 64 to overlay the feature data 80 on the feature data 82 extracted from the frame 1 to frame N−1 images.

The authentication processing unit 10 next calculates, at each position to which the feature data 80 is moved, the degree of consistency between the frame N feature data 80 and the frame 1 to frame N−1 feature data 82. The offset amount of the finger 1 is calculated based on the obtained degree of feature data consistency. The authentication processing unit 10 then determines, as the position of the feature data 80 extracted from the frame N image 64, a point moved from the position of the frame N−1 by the obtained offset amount.

The offset amount of the finger 1 may be calculated through observation of wrinkles on the surface of the finger 1, observation of the outline of the finger 1, or other similar methods. When such methods are employed additionally, the offset amount of the finger 1 can be obtained with high precision.

Here, the authentication processing unit 10 stores coordinates 92 at an upper left end of a position 88 where frame 1 to frame N−1 feature data is pasted. The authentication processing unit 10 moves the position of the frame N feature data 80 such that coordinates 90 at an upper left end of the position of the frame N feature data 80 falls within a given range around the coordinates 92.

In this case, the burden of calculation of the offset amount of the finger 1 imposed on the authentication processing unit 10 can be lessened since the feature data 80 is moved only to limited points.

There is no significant positional change between the frame N image and the frame N−1 image, which are images picked up in succession. The authentication processing unit 10 can therefore move the feature data 80 only to limited points without raising a problem.

Once the position of the frame N feature data 80 is determined, the authentication processing unit 10 pastes together the frame N feature data 80 and the frame 1 to frame N−1 feature data 82.

To be specific, a common image compositing method is used to paste together the frame N feature data 80 and the frame 1 to frame N−1 feature data 82. Examples of the common image compositing method include overwriting a feature pattern, taking a mean value of the feature patterns, and taking the majority of the feature patterns.

The authentication processing unit 10 can obtain the entire vein pattern of the finger 1 by performing the compositing processing (S140) as described above.

Second Embodiment

In a second embodiment of this invention, the input device 2 has a reflective light source.

An authentication system according to the second embodiment of this invention has the same configuration as the authentication system of the first embodiment (FIG. 1) except for the input device 2. Also, the authentication system according to the second embodiment of this invention performs the same processing as the authentication system of the first embodiment (FIG. 7 and others). Descriptions on the common configuration and processing will be omitted.

Figure 10:
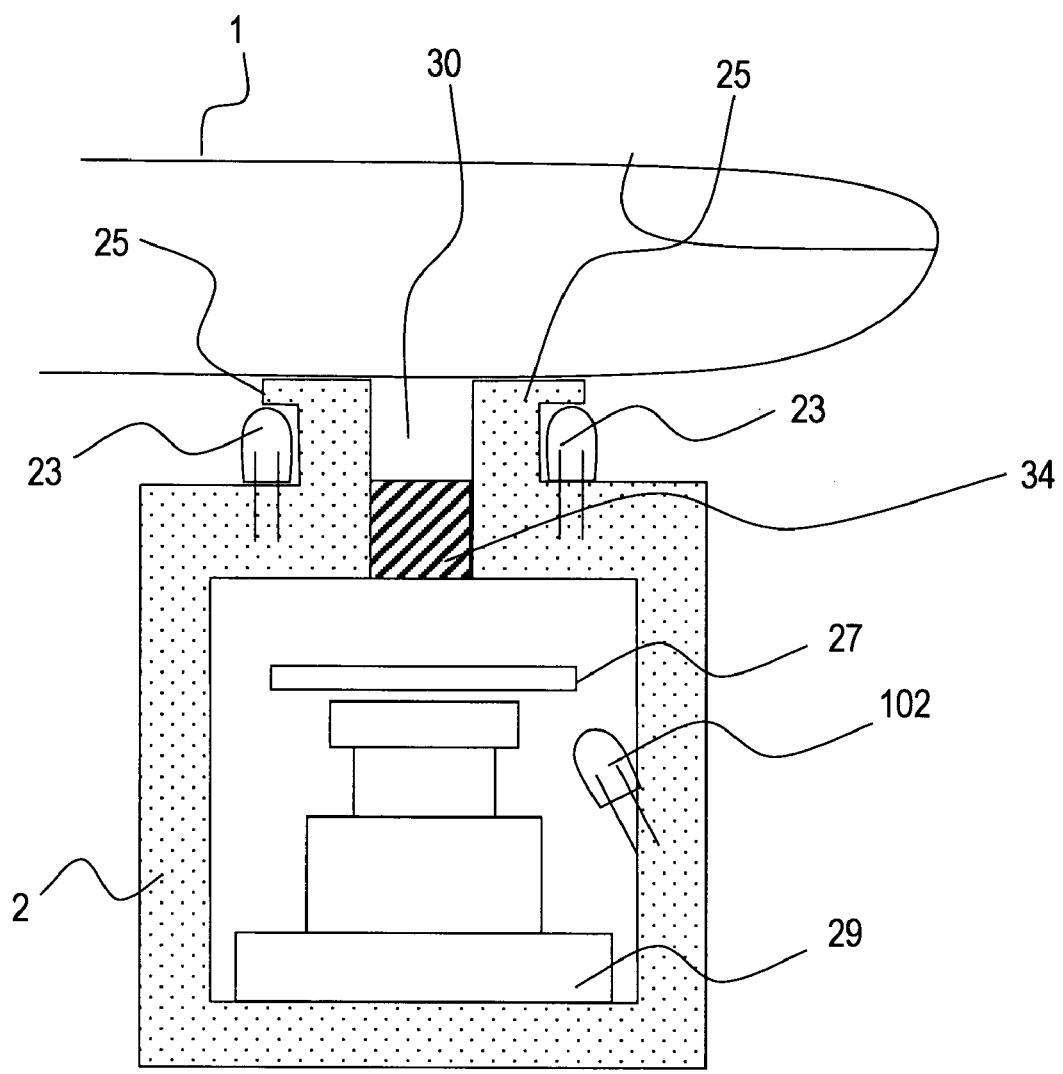
FIG. 10 is a side view of an input device according to a second embodiment of this invention.

FIG. 10 is a side view of the input device 2 according to the second embodiment of this invention.

The input device 2 of the second embodiment has a reflective light source 102. The rest of the configuration of the input device 2 is the same as the input device of the first embodiment (FIGS. 3A, 3B and 3C). The common components are denoted by the same reference numerals and descriptions thereof will be omitted.

In this explanatory diagram, the reflective light source 102 is set near the image pickup device 29 inside the input device 2. The reflective light source 102 is directed toward the opening 30 to irradiate a pickup target portion of the finger 1 with infrared light.

The reflective light source 102 may be installed in an arbitrary place inside the input device 2 as along as the light source 102 can irradiate a pickup target portion of the finger 1 with infrared light. Plural reflective light sources 102 may be installed inside the input device 2.

When the reflective light source 102 irradiates a pickup target portion of the finger 1, the image pickup device 29 picks up infrared light that is reflected from the surface skin of the finger 1 and thus picks up an image of the surface of the finger 1.

From an image of the surface of finger 1 picked up by the image pickup device 29, the authentication processing unit 10 can obtain various kinds of information.

For example, the authentication processing unit 10 obtains from an image picked up by the image pickup device 29 the reflectivity of an object put on the finger rests 25. The authentication processing unit 10 can judge whether the object is the finger 1 or not based on the obtained reflectivity.

The authentication processing unit 10 can also extract information of wrinkles on the surface of the finger 1 from an image picked up by the image pickup device 29. The movement amount of the finger 1 can be calculated from the extracted wrinkle information.

When the light sources 23 are off and the reflective light source 102 is on, the image pickup device 2 picks up an image of the surface of the finger 1. On the other hand, when the light sources 23 are on and the reflective light source 102 is off, the image pickup device 29 picks up a finger vein pattern image.

The input device 2 of this embodiment is a sweep type finger vein authentication device. The finger 1 is therefore moved on the finger rests 25.

The authentication processing unit 10 causes the reflective light source 102 and the light sources 23 to emit light alternately. The image pickup device 29 picks up images of the finger 1 in accordance with the lighting timings of the reflective light source 102 and the light sources 23. The image pickup device 29 can thus pick up an image of the surface of the finger 1 and a finger vein pattern image alternately.

The reflective light source 102 may be used in the finger detecting processing (Step S100 of FIG. 7). In this case, the reflective light source 102 is lit in a regular cycle. The image pickup device 29 picks up an image in a cycle shorter than the lighting cycle of the reflective light source 102. The image pickup device 29 enters the images picked up to the authentication processing unit 10.

The authentication processing unit 10 calculates the luminance values of the entered images. Then, the authentication processing unit 10 compares the luminance values of the images received in succession to one another, to thereby obtain the fluctuation amount in image luminance value. Based on the obtained fluctuation amount in image luminance value, the authentication processing unit 10 judges whether or not the finger 1 is on the finger rests 25.

To be specific, the authentication processing unit 10 judges that the finger 1 is not on the finger rests 25 when the fluctuation amount in image luminance value is smaller than a threshold.

On the other hand, when the fluctuation amount in image luminance value is equal to or larger than the threshold, the authentication processing unit 10 judges that the finger 1 is on the finger rests 25.

As described above, the authentication processing unit 10 can thus perform the finger detecting processing (Step S100 of FIG. 7) using the reflective light source 102.

The authentication system of this embodiment reduces power consumption by using the reflective light source 102, instead of the light sources 23, in the finger detecting processing. This is because the authentication processing unit 10 can detect the finger 1 with infrared light irradiated by the reflective light source 102, which is less intense than the one emitted by the light sources 23.

Third Embodiment

In a third embodiment of this invention, the light sources 23 are set at an angle.

An authentication system according to the third embodiment of this invention has the same configuration as the authentication system of the first embodiment (FIG. 1) except for the input device 2. Also, the authentication system according to the third embodiment of this invention performs the same processing as the authentication system of the first embodiment (FIG. 7 and others). Descriptions on the common configuration and processing will be omitted.

Figure 11A:
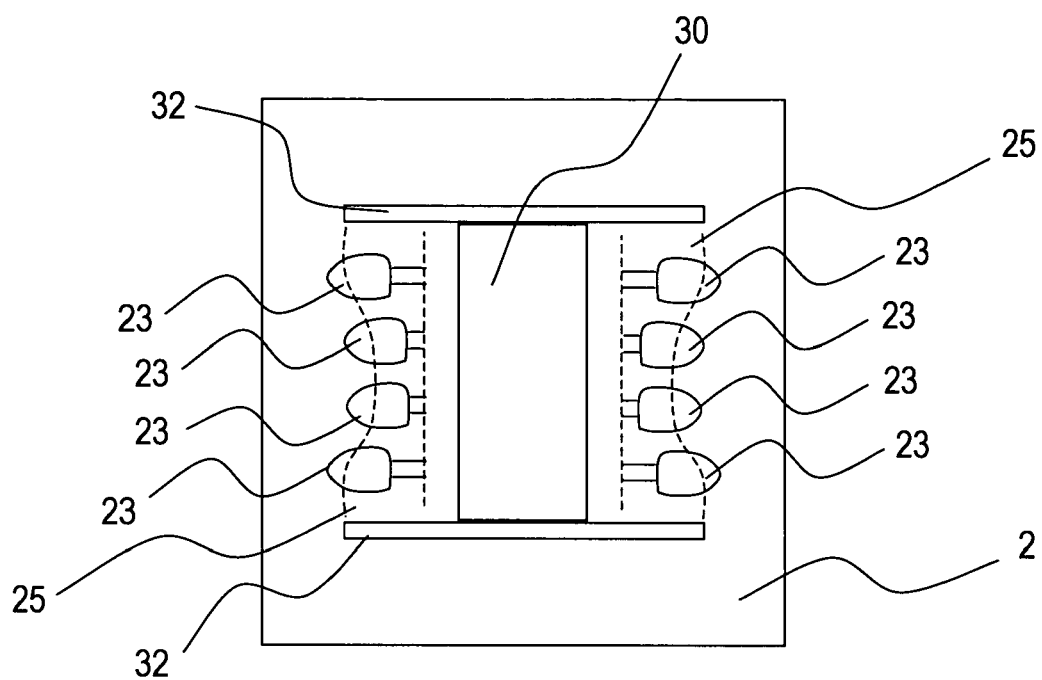
FIG. 11A is a plan view of an input device according to a third embodiment of this invention.
Figure 11B:
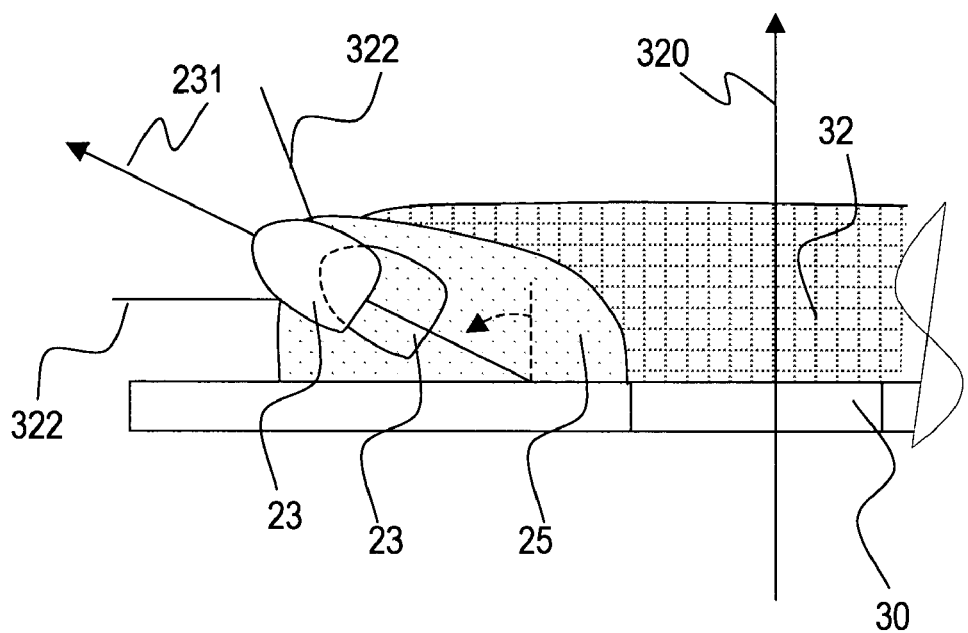
FIG. 11B is an explanatory diagram of a light source in the input device according to the third embodiment of this invention.
Figure 11C:
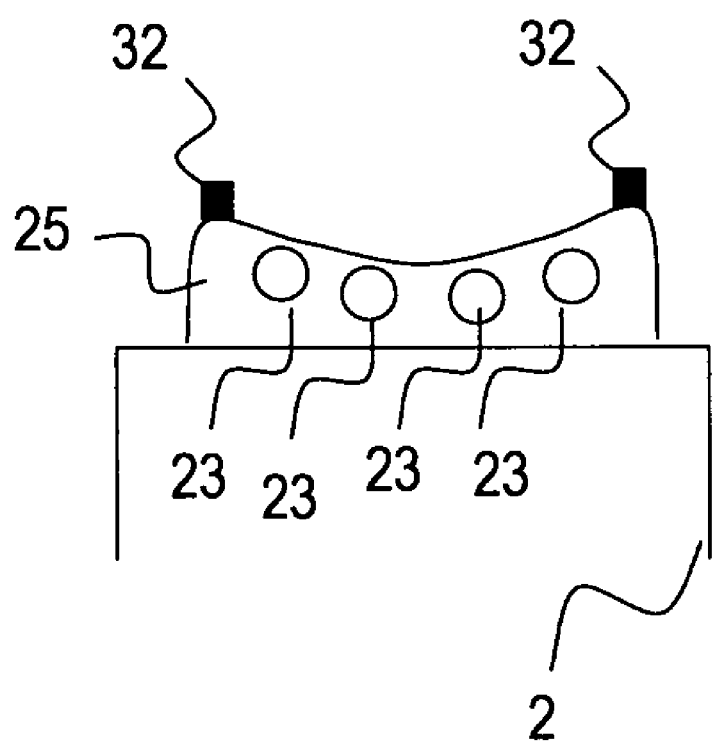
FIG. 11C is a frontal view of the input device according to the third embodiment of this invention.

FIG. 11A is a plan view of the input device 2 according to the third embodiment of this invention. FIG. 11B is an explanatory diagram of the light sources 23 in the input device 2 according to the third embodiment of this invention. FIG. 11C is a frontal view of the input device 2 according to the third embodiment of this invention.

The input device 2 of the third embodiment has the same configuration as the input device of the first embodiment (FIGS. 3A, 3B and 3C) except for the light sources 23 and the finger rests 25. The common components are denoted by the same reference numerals and descriptions thereof will be omitted.

The light sources 23 emit divergent infrared light (infrared light with directivity). The light sources 23 are set at an angle opposite to the opening 30.

The light sources 23 are tilted by, for example, 60° with respect to the image pickup direction 320 of the image pickup device 29. This means that the light sources 23 emit light having the optical axis 231 in a direction tilted by 60° with respect to the image pickup direction 320 of the image pickup device 29. Here, the image pickup direction 320 is a direction of an optical axis along which the image pickup device 29 picks up an image. In this way, infrared light emitted from the light sources 23 is directed toward a direction opposite to the opening 30.

The finger rests 25 are set such that the divergence of infrared light from the light sources 23 does not include the image pickup direction. In other words, the finger rests 25 are set such that every component of infrared light emitted from the light sources 23 travels toward a direction opposite to the opening 30. The divergence of infrared light emitted from the light sources 23 is a range between the border lines 322.

The finger rests 25 of this embodiment do not need to cover to a half of the upper portions of the light sources 23 since the light sources 23 are tilted toward the image pickup direction. Depending on the divergence of infrared light from the light sources 23, the finger rests 25 may not cover the upper portions of the light sources 23 at all.

In this embodiment, infrared light emitted from the light sources 23 enters the finger 1 at a point further from the opening 30 as compared with the first embodiment. This provides an advantage that an image picked up by the image pickup device 29 has a uniform luminance value.

Fourth Embodiment

In a fourth embodiment of this invention, the finger rests 25 have pits.

An authentication system according to the fourth embodiment of this invention has the same configuration as the authentication system of the first embodiment (FIG. 1) except for the input device 2. Also, the authentication system according to the fourth embodiment of this invention performs the same processing as the authentication system of the first embodiment (FIG. 7 and others). Descriptions on the common configuration and processing will be omitted.

Figure 12:
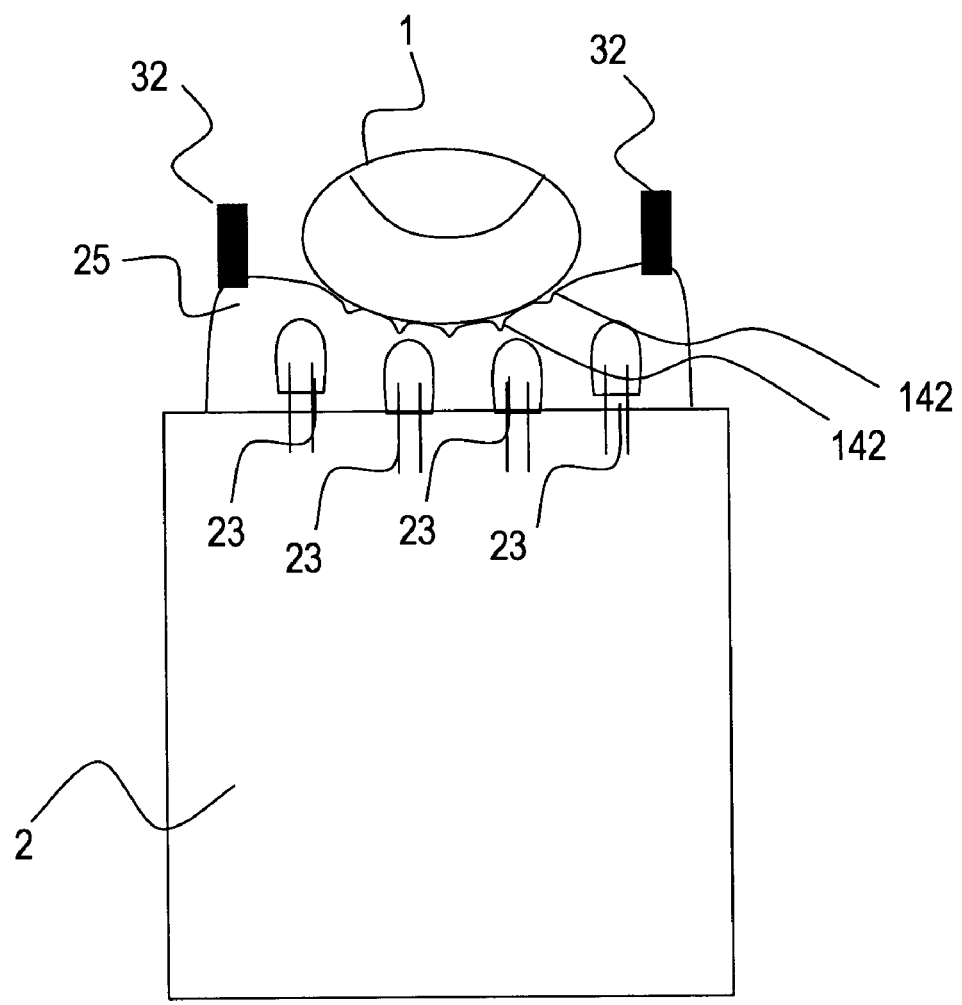
FIG. 12 is a frontal view of an input device according to a fourth embodiment of this invention.

FIG. 12 is a frontal view of the input device 2 according to the fourth embodiment of this invention.

The input device 2 of the fourth embodiment has the same configuration as the input device of the first embodiment (FIGS. 3A, 3B and 3C) except for the finger rests 25. The common components are denoted by the same numbers and descriptions thereof will be omitted.

The finger rests 25 have pits 142 in a surface that comes into contact with the finger 1. The pits 142 run in the longitudinal direction of the finger 1. The pits 142 do not put pressure on the finger 1 and allow the blood in the finger 1 to flow freely.

When a user presses the finger 1 harder than necessary against the finger rests 25 while moving the finger 1, the pressure between the finger 1 and the finger rests 25 pushes the blood away from the pickup target surface of the finger 1, unless the finger rests 25 have the pits 142. Then, an image picked up by the image pickup device 29 will not show a clear finger vein pattern.

When the finger rests 25 have the pits 142, the blood runs along the pits 142. This enables the image pickup device 29 to pick up a clear image of a finger vein pattern even when a user presses the finger 1 harder than necessary against the finger rests 25.

Fifth Embodiment

In a fifth embodiment of this invention, finger rests and light shielding members are separate components.

An authentication system according to the fifth embodiment of this invention has the same configuration as the authentication system of the first embodiment (FIG. 1) except for the input device 2. Also, the authentication system according to the fifth embodiment of this invention performs the same processing as the authentication system of the first embodiment (FIG. 7 and others). Descriptions on the common configuration and processing will be omitted.

Figure 13:
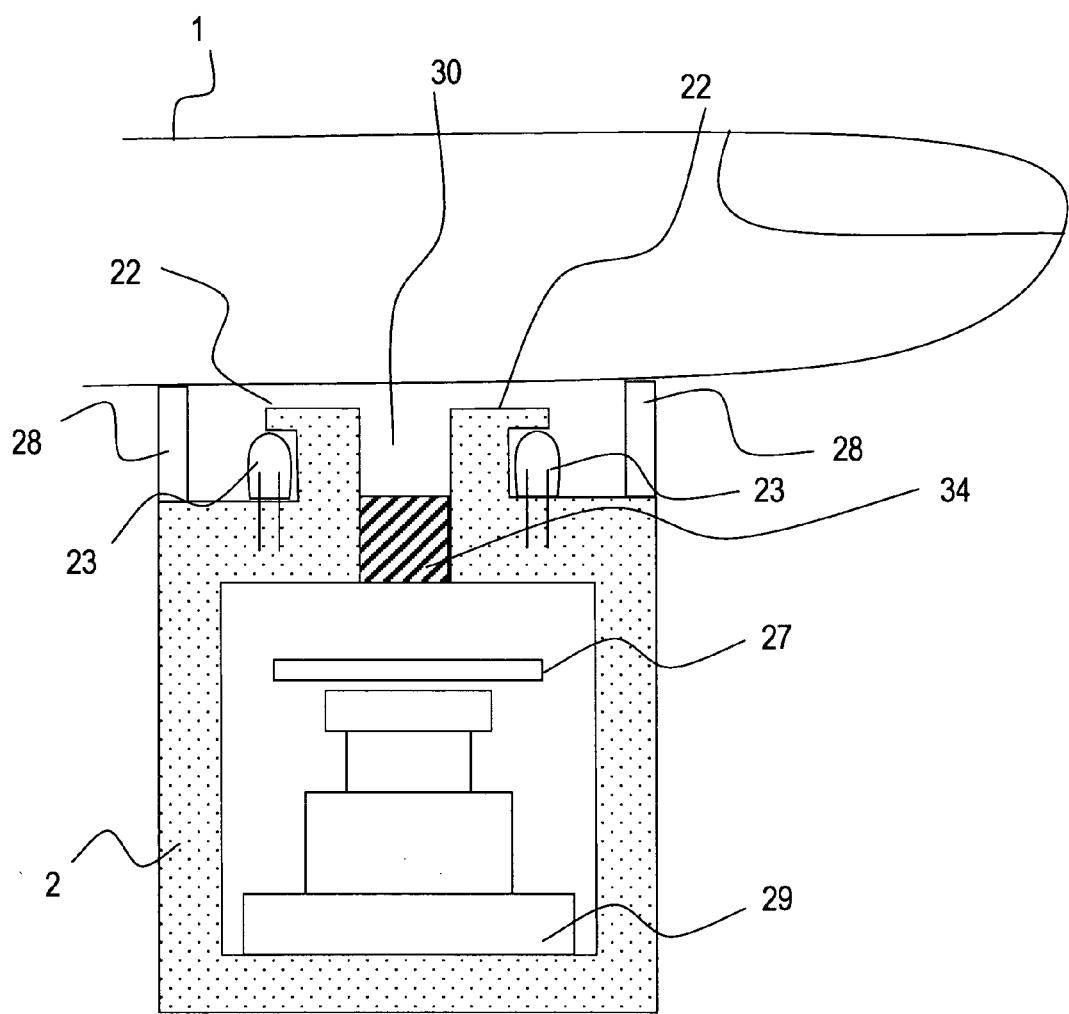
FIG. 13 is a side view of an input device according to a fifth embodiment of this invention.

FIG. 13 is a side view of the input device 2 according to the fifth embodiment of this invention.

The input device 2 of the fifth embodiment has the same configuration as the input device of the first embodiment (FIGS. 3A, 3B and 3C) except for light shielding members 22 and finger rests 28. The common components are denoted by the same numbers and descriptions thereof will be omitted.

The input device 2 is provided with the light shielding members 22 and the finger rests 28 in place of the finger rests 25 of the first embodiment.

The finger rests 25 of the first embodiment double as light shielding members by being formed from a material that does not transmit infrared light.

In this embodiment, the light shielding members 22 are set between the light sources 23 and the opening 30. The light shielding members 22 are formed from a material that does not transmit infrared light.

The finger rests 28 are set opposite to the opening 30 with respect to the light sources 23. The finger rests 28 are where the finger 1 is put for authentication. The material of the finger rests 28 may be or may not be transmissive of infrared light.

Sixth Embodiment

Authentication according to a sixth embodiment of this invention is made without requiring the finger 1 to move.

An authentication system according to the sixth embodiment of this invention has the same configuration as the authentication system of the first embodiment (FIG. 1) except for the input device 2. Descriptions on the common configuration will be omitted.

Figure 14:
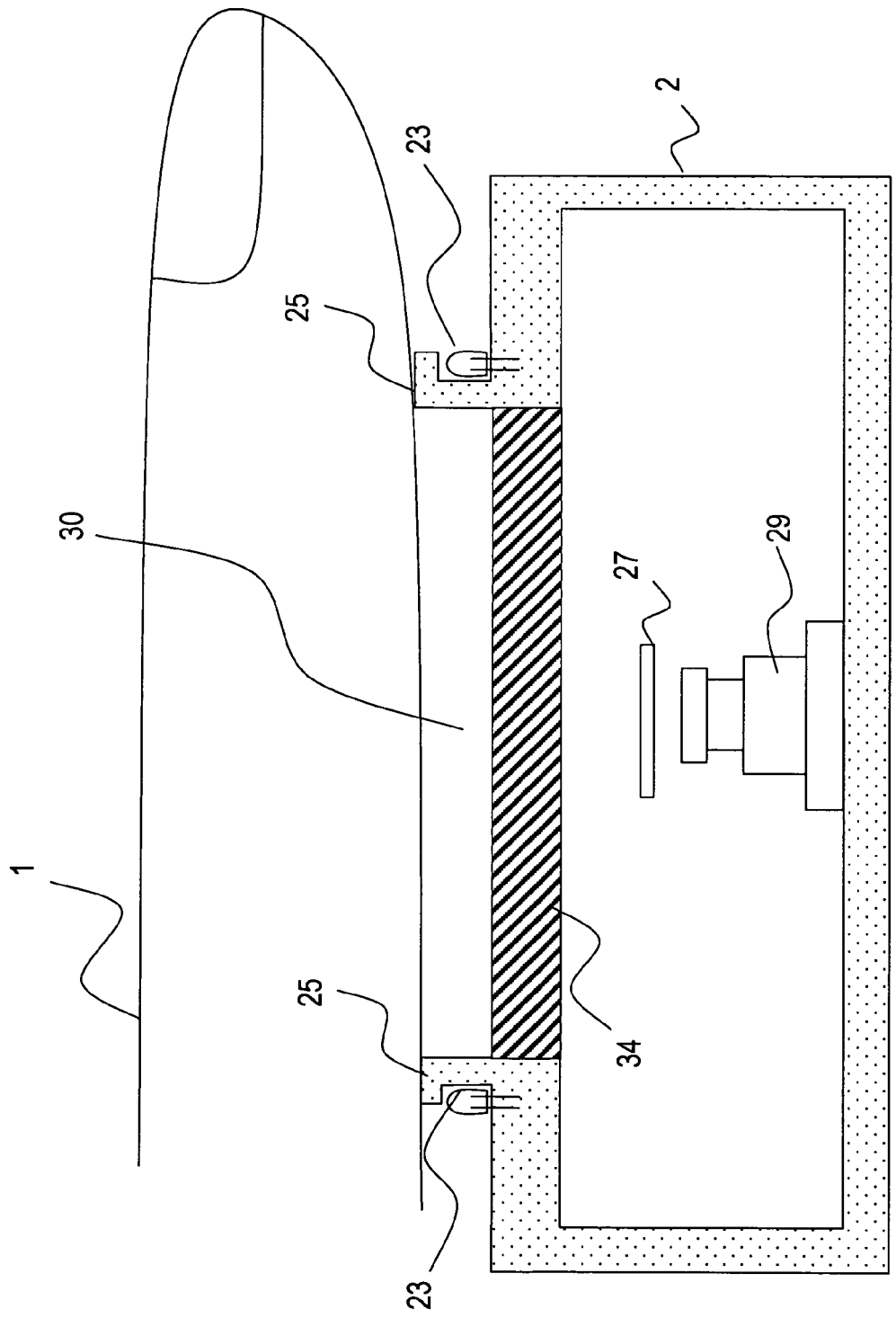
FIG. 14 is a side view of an input device according to a sixth embodiment of this invention.

FIG. 14 is a side view of the input device 2 according to the sixth embodiment of this invention.

The input device 2 of the sixth embodiment has the same configuration as the input device of the first embodiment (FIGS. 3A, 3B and 3C) except for the size of the opening 30. The common components are denoted by the same numbers and descriptions thereof will be omitted.

Two finger rests 25 are set such that the opening 30 is interposed between them. The opening 30 is wider in the longitudinal direction of the finger 1 as compared with the opening of the first embodiment (FIG. 3A). The opening 30 is wide enough for the image pickup device 29 to pick up a finger vein pattern image necessary for authentication.

The authentication system of the sixth embodiment in which the opening 30 is wide does not need users to move the finger 1. A user only has to put the finger on the finger rests 25 to be checked for authenticity.

Light amount control processing according to this embodiment will be described.

Figure 15:
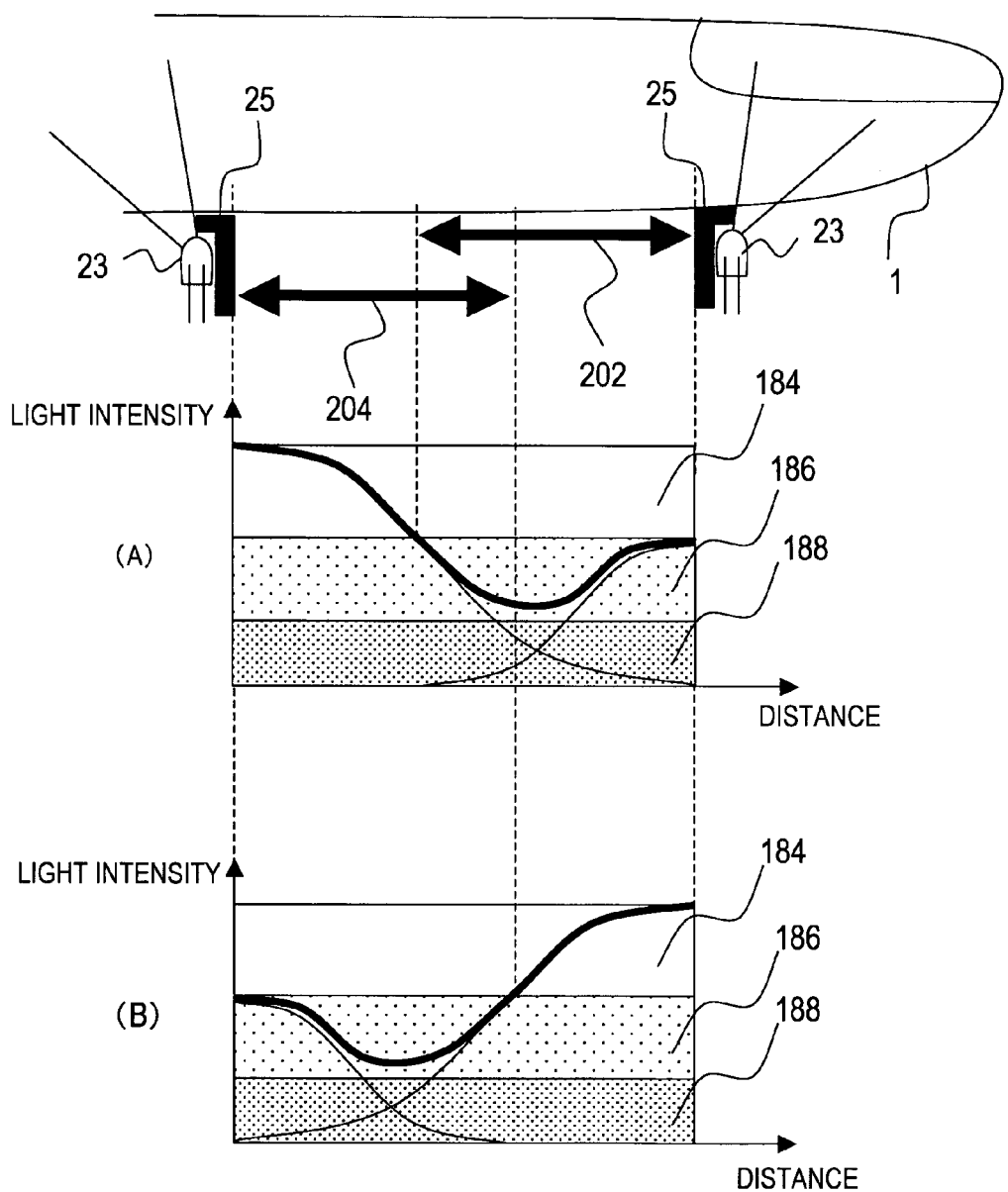
FIG. 15 is an explanatory diagram showing a relation between a distance from a light source and a luminance value of a finger vein pattern image according to the sixth embodiment of this invention.

FIG. 15 is an explanatory diagram of a relation between the distance from the light sources 23 and the luminance value of a finger vein pattern image of the sixth embodiment.

A graph of this explanatory diagram shows a relation between the distance from the light sources 23 and the luminance value of a finger vein pattern image. The graph is of when there are the light sources 23 on the fingertip side and on the root side of the finger 1. The graph is obtained by making a mirror reverse of the graph (of FIG. 6) which is of when the light sources 23 are provided to only one side, and compositing it with the original graph.

A luminance value is classified into any one of the high luminance range 184, the visible range 186, and the low luminance range 188.

When an image has a luminance value in the high luminance range 184, the authentication processing unit 10 cannot obtain finger vein pattern information from the image, since this image is saturated with light. When an image has a luminance value in the visible range 186, the authentication processing unit 10 can obtain finger vein pattern information from the image. When an image has a luminance value in the low luminance range 188, the authentication processing unit 10 cannot obtain finger vein pattern information from the image, since light in this image is too weak.

In the input device 2 of this embodiment where the opening 30 is wide, the authentication processing unit 10 sometimes cannot make the visible range 186 contain the entire area of the opening 30 no matter how the light amount of the light sources 23 on both sides is controlled.

The authentication processing unit 10 in this case changes the light amount of the light sources 23 on the root side of the finger 1 and the light amount of the fingertip side light sources 23 in a time-series manner. The image pickup device 29 picks up an image at each intensity of light. The image picked up partially has an optimum brightness. The authentication processing unit 10 obtains an image that has an optimum brightness throughout the entire area by compositing images picked up by the image pickup device 29.

Specific processing will be described below.

The authentication processing unit 10 first makes the finger root side light sources 23 to emit intense light and the fingertip side light sources 23 to emit weak light.

The image pickup device 29 picks up an image in this state. The image has a luminance value as indicated by a graph (A) of FIG. 15. Accordingly, the image looks as shown in FIG. 16A.

Figure 16A:
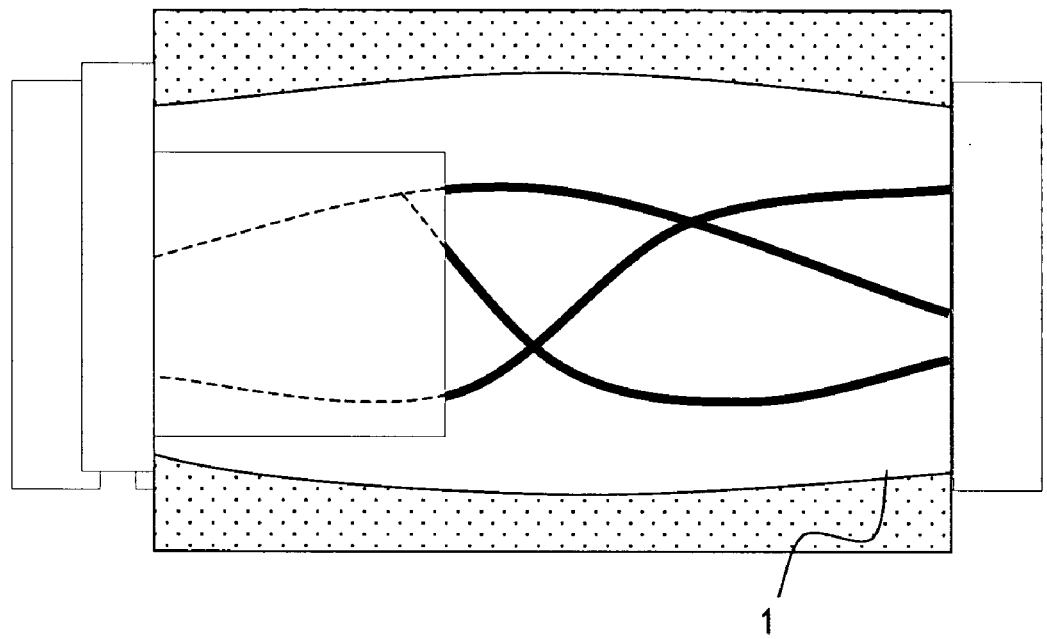
FIG. 16A is an explanatory diagram of an image picked up when a finger root side light source is intense according to the sixth embodiment of this invention.

FIG. 16A is an explanatory diagram of an image picked up when the light sources 23 on the root side of the finger 1 emit intense light according to the sixth embodiment of this invention.

An image picked up by the image pickup device 29 when the light sources 23 on the root side of the finger 1 emit intense light has an optimum brightness in a fingertip side area that is equal to or larger than a half of the whole image. On the root side of the finger 1, however, the image is partially saturated with light.

Therefore, the authentication processing unit 10 makes the finger root side light sources 23 to emit less intense light and the fingertip side light sources 23 to emit intense light.

The image pickup device 29 picks up an image in this state. The image has a luminance value as indicated by a graph (B) of FIG. 15. Accordingly, the image looks as shown in FIG. 16B.

Figure 16B:
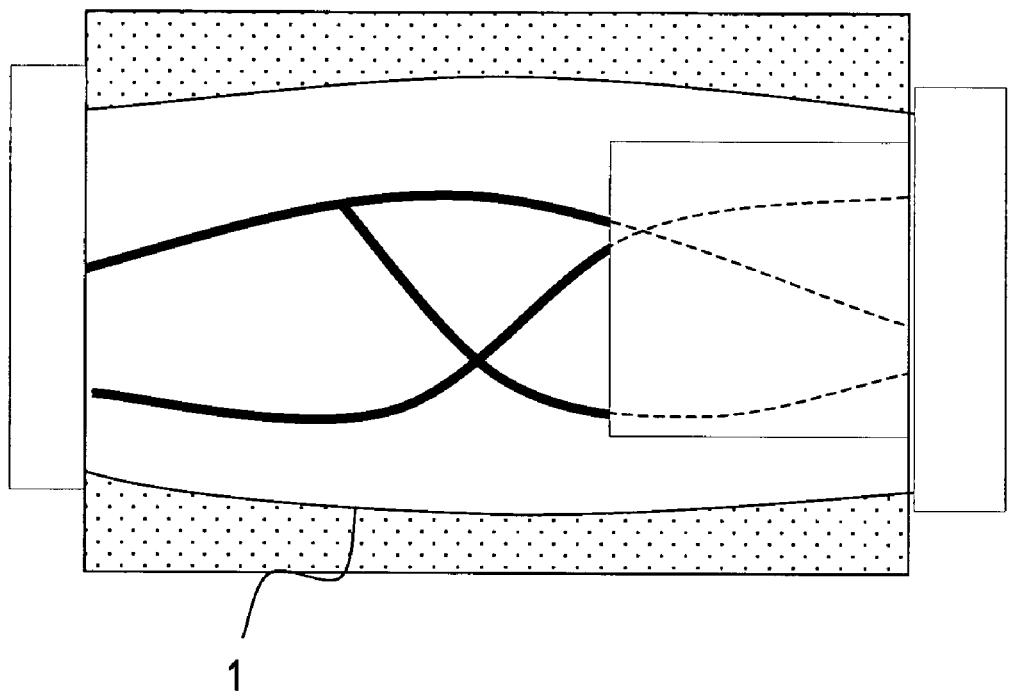
FIG. 16B is an explanatory diagram of an image picked up when a fingertip side light source is intense according to the sixth embodiment of this invention.

FIG. 16B is an explanatory diagram of an image picked up when the fingertip side light sources 23 emit intense light according to the sixth embodiment of this invention.

An image picked up by the image pickup device 29 when the fingertip side light sources 23 emit intense light has an optimum brightness in a finger root side area that is equal to or larger than a half of the whole image. On the fingertip side, however, the image is partially saturated with light.

The authentication processing unit 10 composites these two images picked up by the image pickup device 29 (FIG. 16A and FIG. 16B).

Figure 16C:
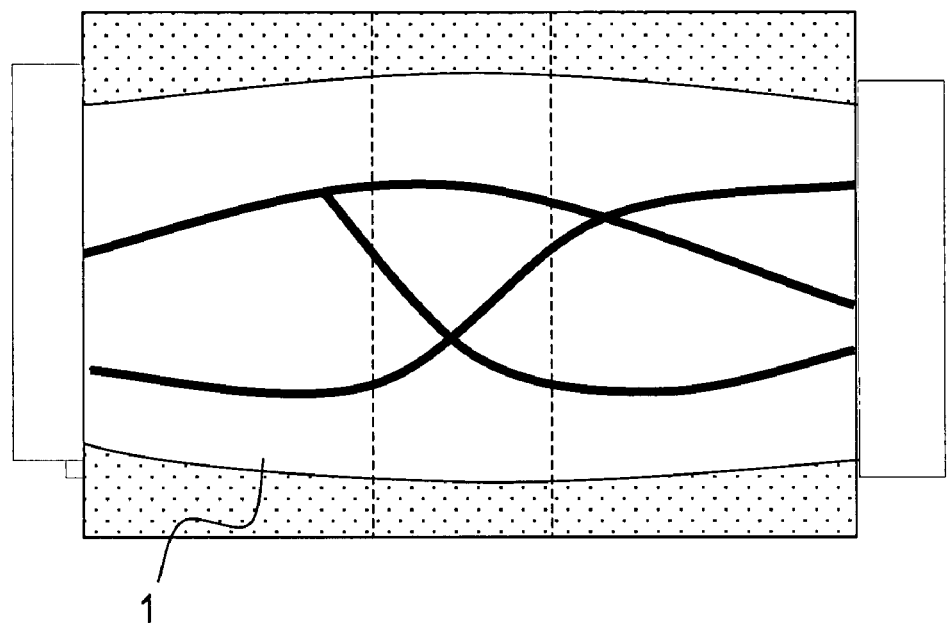
FIG. 16C is an explanatory diagram of an image composited by an authentication processing unit according to the sixth embodiment of this invention.

FIG. 16C is an explanatory diagram of an image composited by the authentication processing unit 10 according to the sixth embodiment of this invention.

The authentication processing unit 10 composites the image of the fingertip side area shown in FIG. 16A with the image of the finger root side area shown in FIG. 16B. The image of the fingertip side area is equal to or larger than a half of the whole picked up image and has an optimum brightness. The image of the finger root side is equal to or larger than a half of the whole picked up image and has an optimum brightness. The authentication processing unit 10 thus obtains an image that has an optimum brightness throughout the entire area shown in this explanatory diagram.

The authentication processing unit 10 may obtain an image that has an optimum brightness throughout its entire area by compositing two or more images.

In this case, the authentication processing unit 10 makes the light sources 23 on one side emit progressively more intense light and the light sources 23 on the other side to emit progressively less intense light. The image pickup device 29 picks up an image at each intensity of light. In images picked up in this manner, an area that has an optimum brightness moves gradually. The authentication processing unit 10 obtains an image that has an optimum brightness throughout the entire area by compositing images picked up by the image pickup device 29.

The image pickup device 29 of the authentication processing unit 10 according to the sixth embodiment picks up an image of the entire finger 1. The authentication processing unit 10 accordingly corrects the tilt of the finger 1 and cuts off the background, which makes it necessary to detect the outline of the finger 1.

The authentication processing unit 10 uses a common image processing method to detect the outline of the finger 1. Examples of the common image processing method include edge enhancement and a profile line tracing.

The authentication processing unit 10 may also compare plural images to detect the outline of the finger 1.

To be specific, the authentication processing unit 10 compares an image picked up when the light sources 23 emit intense light against an image picked up when the light sources 23 are off, and detects an area where there is a large change in luminance value as a finger area. The authentication processing unit 10 can thus detect the outline of the finger 1 stably.

The authentication system of the sixth embodiment is capable of obtaining a clear finger vein pattern when the finger 1 on the finger rests 25 is bent as well as when the finger 1 is resting correctly on the finger rests 25. This is because the same principle that the infrared light from the light sources 23 is scattered inside the finger 1 and then travels to the outside applies to both cases.

However, when the finger 1 on the finger rests 25 is bent, the authentication processing unit 10 calculates the distance between the finger 1 and the device based on the detected outline of the finger 1. The authentication processing unit 10 uses the obtained distance between the finger 1 and the device to correct the magnification. The authentication processing unit 10 can thus reduce the influence of a bend of the finger 1 over the crosschecking processing. In other words, users are allowed to bend the finger 1 to a certain degree, and it improves the user-friendliness of the system.

Furthermore, the authentication system of the sixth embodiment can obtain a finger vein pattern even when the finger 1 is not in contact with the finger rests 25. The mechanism of this is the same as how a clear finger vein pattern can be obtained when the finger 1 is lifted in the first embodiment (FIGS. 5A and 5B).

The authentication system of the sixth embodiment can authenticate a user without requiring the user to bring the finger 1 into contact with the finger rests 25. Thus, reluctant users may feel toward contact can be assuaged.

The sixth embodiment is applicable to the second to fifth embodiments by widening the opening 30.

Seventh Embodiment

In a seventh embodiment of this invention, an authentication system is mounted to a portable information terminal.

Figure 17A:
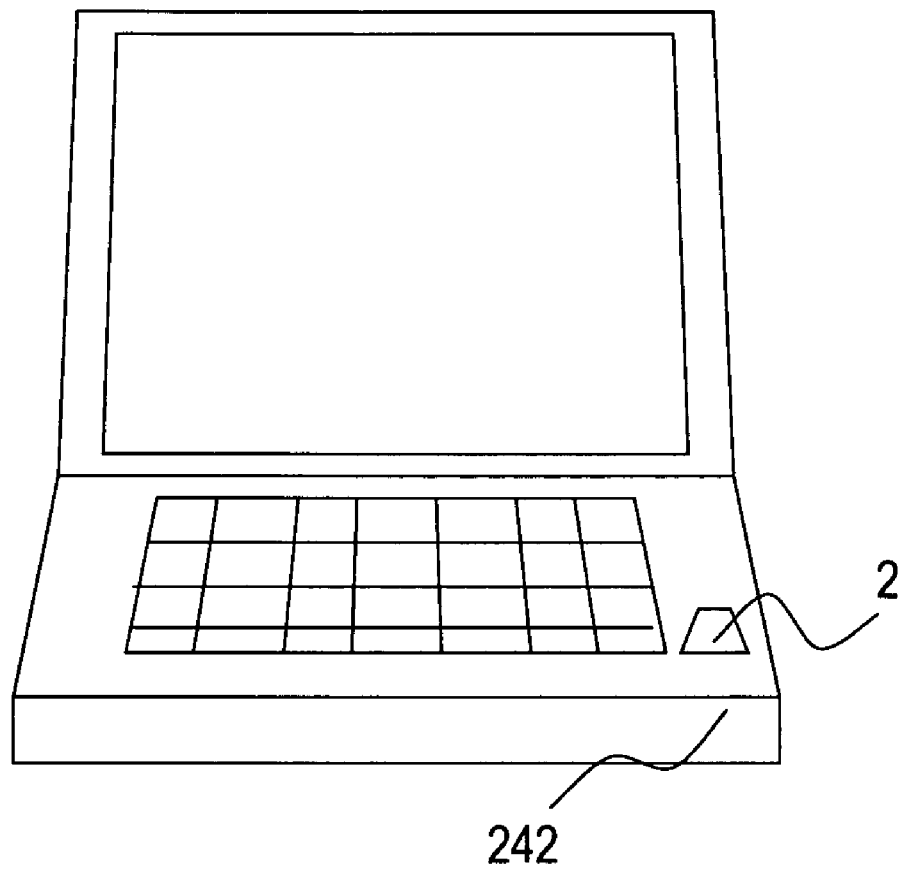
FIG. 17A is an explanatory diagram of a portable information terminal according to a seventh embodiment of this invention.

FIG. 17A is an explanatory diagram of a portable information terminal 242 according to the seventh embodiment of this invention.

The portable information terminal 242 is mounted with an authentication system, which can be any one of the authentication systems of the first to sixth embodiments.

The input device 2 of the authentication system is set such that the finger rests 25 are exposed on a surface of the portable information terminal 242. The input device 2 may be placed on a side face of the portable information terminal 242.

The authentication system mounted to the portable information terminal 242 has the same configuration as the authentication system of the first embodiment (FIG. 1) except for the input device 2. The authentication system mounted to the portable information terminal 242 performs the same processing as the authentication system of the first embodiment (FIG. 7 and others). Descriptions on the common configuration and processing will be omitted.

Figure 17B:
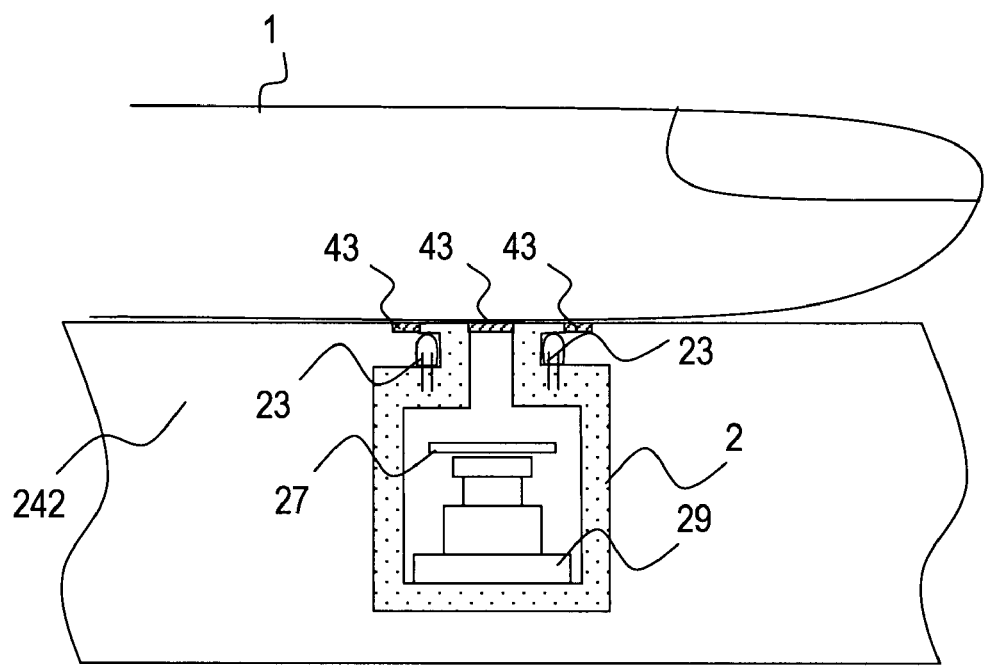
FIG. 17B is a side view of an input device that is mounted to the portable information terminal according to the seventh embodiment of this invention.

FIG. 17B is a side view of the input device 2 that is mounted to the portable information terminal 242 according to the seventh embodiment of this invention.

The input device 2 has the same configuration as the input device of the first embodiment (FIGS. 3A, 3B and 3C) except that the input device 2 of this embodiment has light source light windows 43. The common components are denoted by the same numbers and descriptions thereof will be omitted.

The light source light windows 43 are set on the same plane as the surface of the portable information terminal 242. The light source light windows 43 cover the upper portions of the light sources 23 and the top of the opening 30. The material of the light source light windows 43 is transmissive of infrared light.

The finger rests 25 may have a curved, dipped shape, or a planar shape. When the finger rests 25 have a planar shape, where to put the finger 1 may be printed on their surfaces, or the surfaces may be formed from a material having different feel of touch. In this way, users understand where to put the finger 1 and in which direction the finger 1 is to be moved.

Eighth Embodiment

In an eighth embodiment of this invention, an authentication system is mounted to a portable information terminal.

Figure 18A:
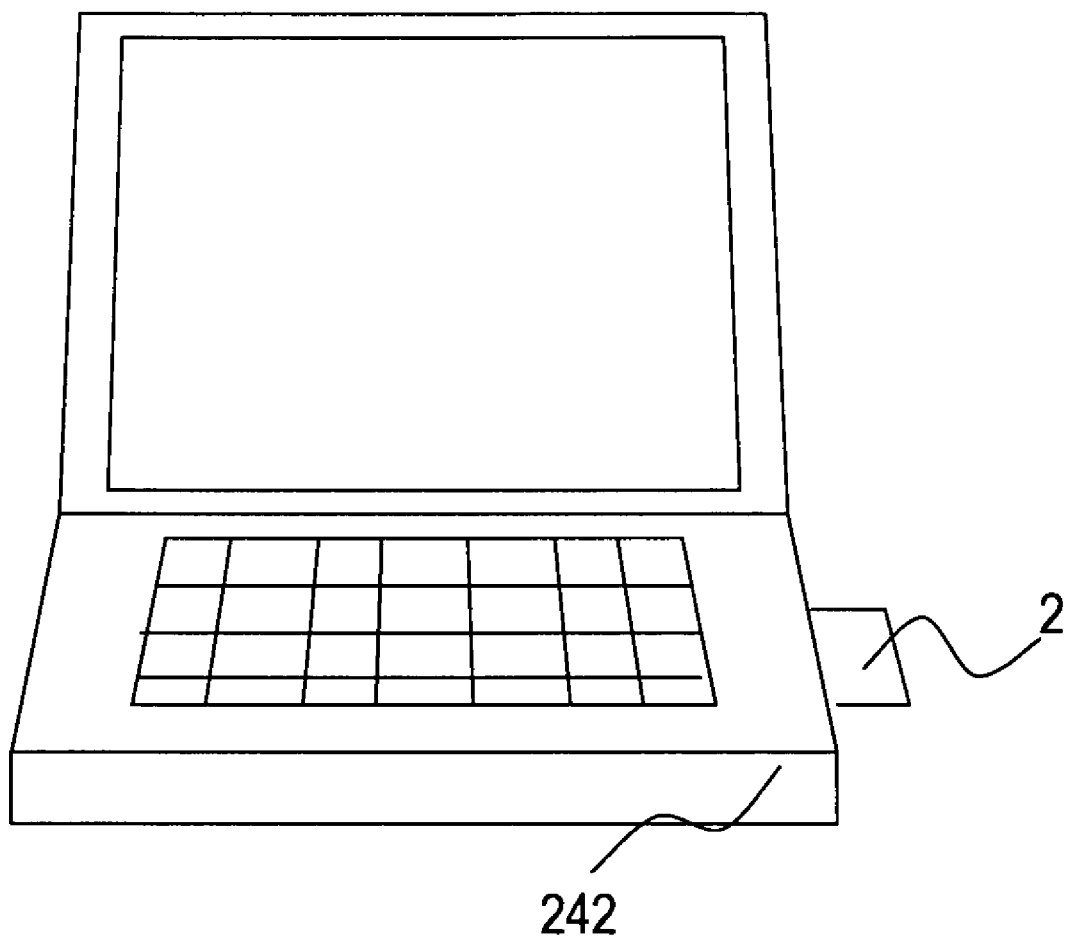
FIG. 18A is an explanatory diagram of a portable information terminal according to an eighth embodiment of this invention.

FIG. 18A is an explanatory diagram of the portable information terminal 242 according to the eighth embodiment of this invention.

The portable information terminal 242 is mounted with an authentication system, which can be any one of the authentication systems of the first to sixth embodiments.

The input device 2 of the authentication system is retractably installed in a side face of the portable information terminal 242. This explanatory diagram shows the portable information terminal 242 with the input device 2 pulled out. The input device 2 is moved leftward through control by software or physical control, to be retracted inside the portable information terminal 242.

In this way, an authentication system can be mounted to the portable information terminal 242 when it is not possible to place the input device 2 of the authentication system on a surface of the portable information terminal 242.

The authentication system mounted to the portable information terminal 242 has the same configuration as the authentication system of the first embodiment (FIG. 1) except for the input device 2. The authentication system mounted to the portable information terminal 242 performs the same processing as the authentication system of the first embodiment (FIG. 7 and others). Descriptions on the common configuration and processing will be omitted.

Figure 18B:
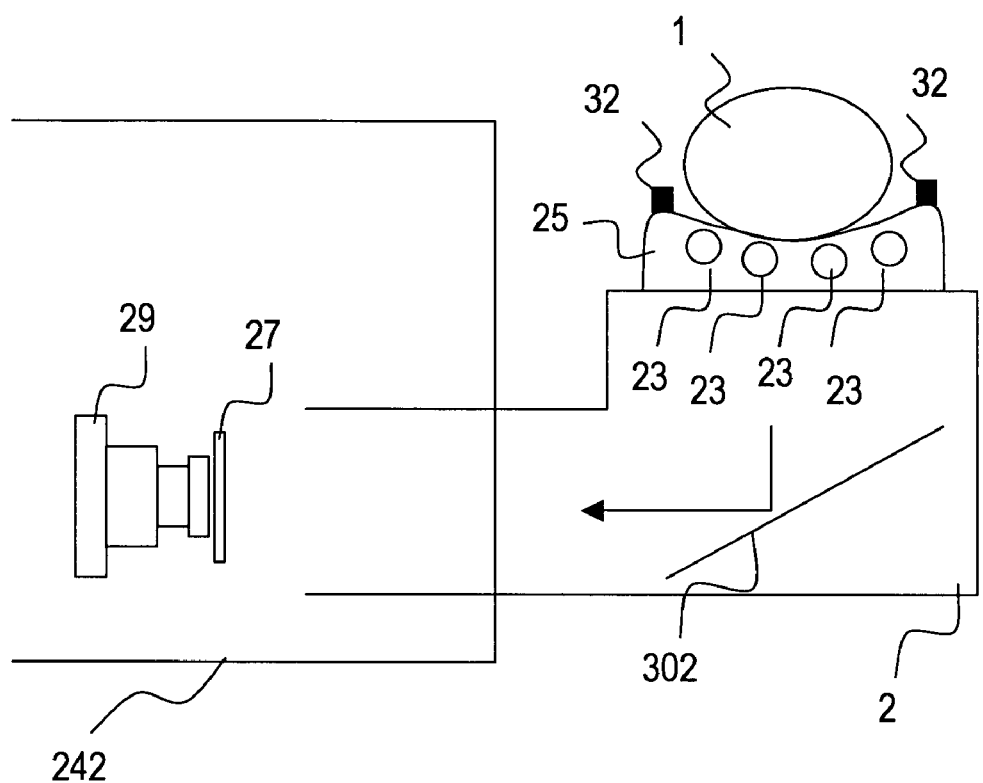
FIG. 18B is a frontal view of an input device that is mounted to the portable information terminal according to the eighth embodiment of this invention.

FIG. 18B is a frontal view of the input device 2 that is mounted to the portable information terminal 242 according to the eighth embodiment of this invention.

The input device 2 has the same configuration as the input device of the first embodiment (FIGS. 3A, 3B and 3C) except that the input device 2 of this embodiment has a reflector 302, and except for the positions of the infrared transmitting filter 27 and the image pickup device 29. The common components are denoted by the same numbers and descriptions thereof will be omitted.

The reflector 302 is set inside the input device 2. The reflector 302 is, for example, a prism or an optical fiber, and changes the path of infrared light.

The image pickup device 29 is set inside the portable information terminal 242 facing toward the reflector 302. The infrared transmitting filter 27 is set between the image pickup device 29 and the reflector 302.

The image pickup device 29 picks up infrared light that enters the input device 2 from outside and travels through the opening 30, the reflector 302 and the infrared transmitting filter 27. In short, the image pickup device 29 picks up infrared light whose path has been changed by the reflector 302.

Ninth Embodiment

In a ninth embodiment of this invention, an authentication system is mounted to a door knob.

Figure 19A:
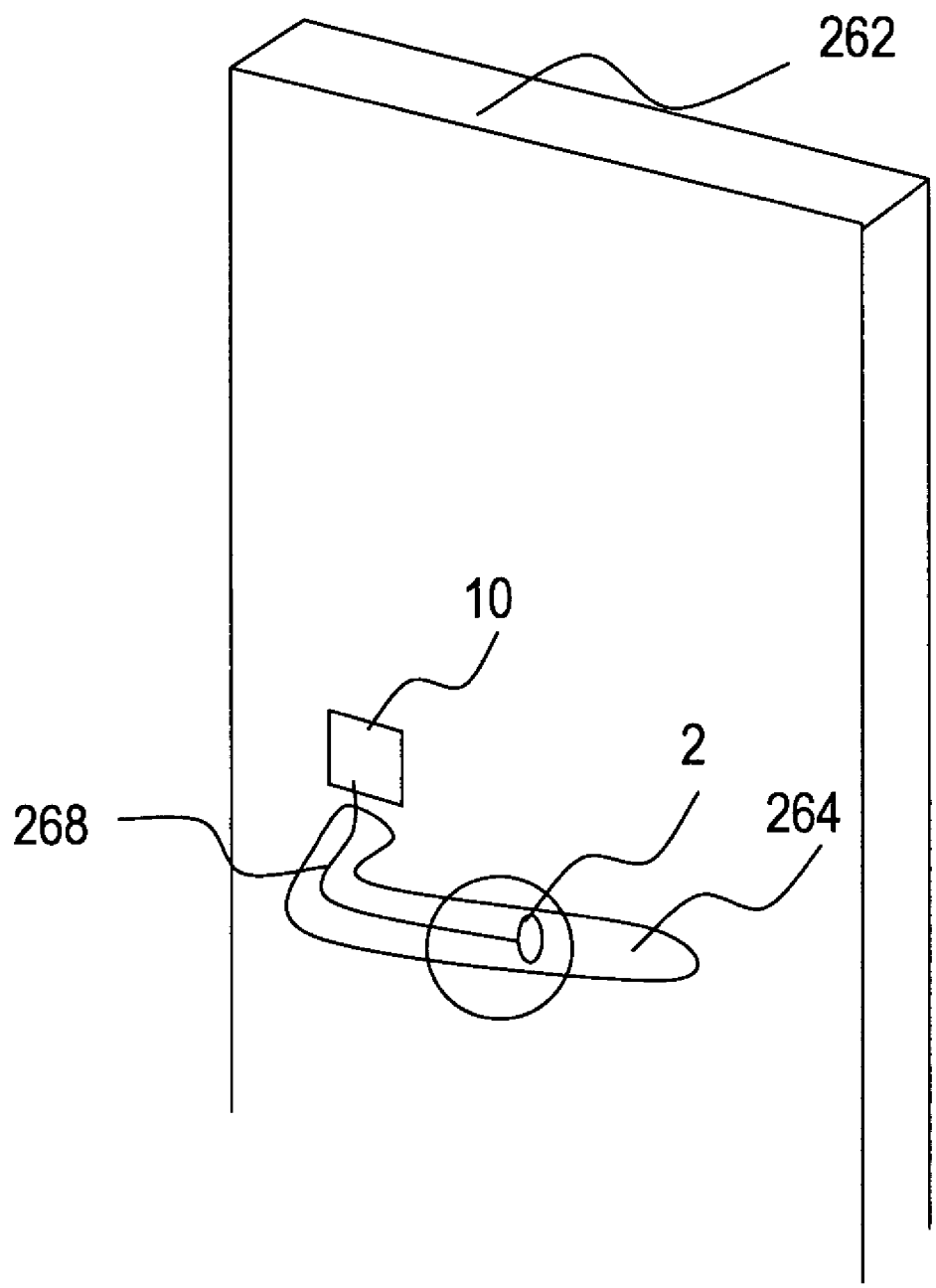
FIG. 19A is an explanatory diagram of a door knob according to a ninth embodiment of this invention.
Figure 19B:
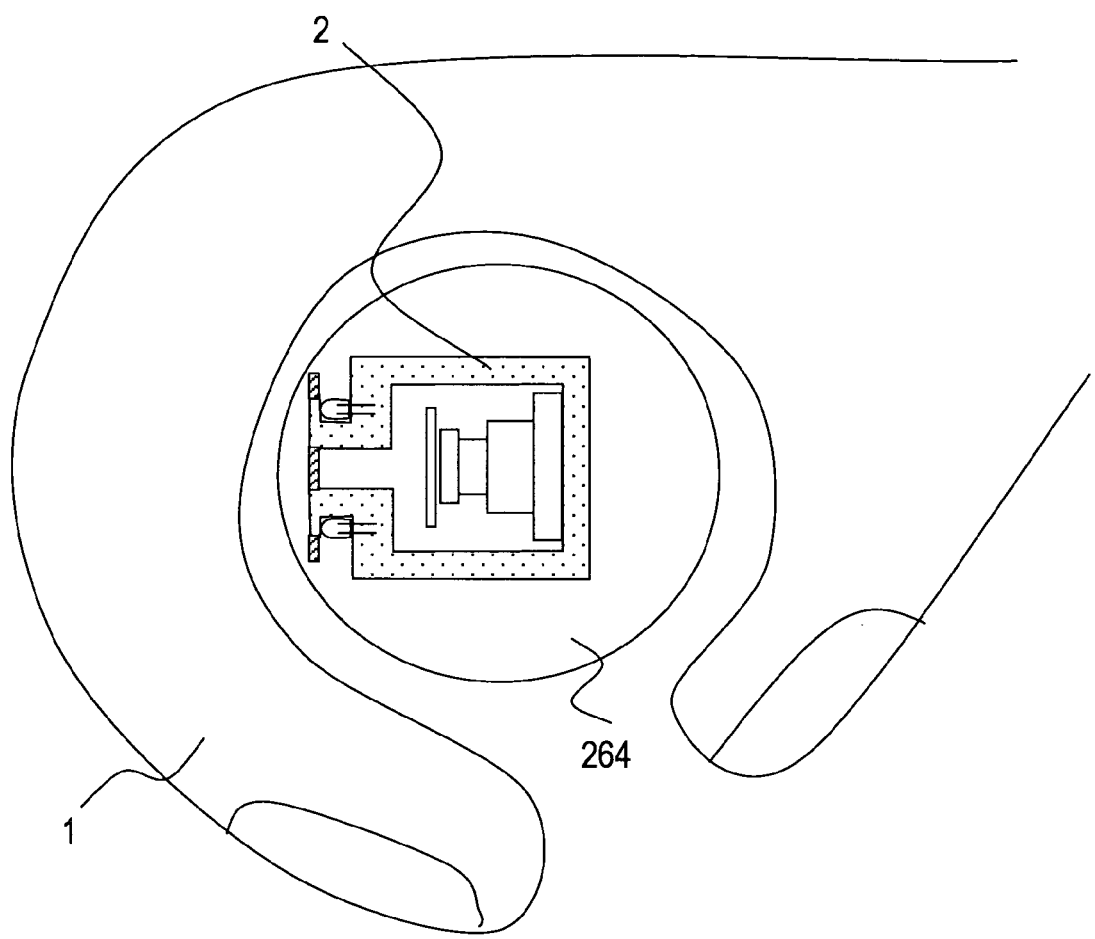
FIG. 19B is a side view of an input device that is mounted to the door knob according to the ninth embodiment of this invention.

FIG. 19A is an explanatory diagram of a knob 264 to a door 262 according to the ninth embodiment of this invention. FIG. 19B is a side view of the input device 2 that is mounted to the knob 264 of the door 262 according to the ninth embodiment of this invention.

The knob 264 to the door 262 is mounted with an authentication system, which can be any one of the authentication systems of the first to sixth embodiments.

That is, the input device 2, the authentication processing unit 10, and a communication cable 268 are installed in the knob 264. The communication cable 268 connects the input device 2 and the authentication processing unit 10 to each other.

The authentication system mounted to the knob 264 has the same configuration as the authentication system of the first embodiment (FIG. 1) except for the input device 2. The authentication system mounted to the knob 264 performs the same processing as the authentication system of the first embodiment (FIG. 7 and others). Descriptions on the common configuration and processing will be omitted.

A user grips the knob 264 to open the door 262. At this point, the input device 2 mounted to the knob 264 obtains a finger vein pattern image and sends the obtained image to the authentication processing unit 10.

The authentication processing unit 10 performs the authentication processing on the image received from the input device 2. In the case where the image matches authentication data stored in the storage 14, the authentication processing unit 10 unlocks the door 262.

Accordingly, users only have to perform operation to pull the knob 264.

The authentication system of this embodiment attains authentication of a user through a natural movement of the user, and therefore is improved in user-friendliness.

The authentication system of this embodiment may be mounted to cellular phones, steering wheels of automobiles, grips of motorcycles, and the like, in a manner similar to the knob 264 of the door 262. When the authentication system is mounted to components that are gripped by users, a user can be authenticated through a natural movement of the user.

Moreover, since the authentication system completes authentication of a user as soon as the user grips a component to which the authentication system is mounted, the authentication system can assist the next movement of the user utilizing the authentication result.

For instance, upon completing authentication, the authentication system assists the user's movement to open the door 262. To be specific, the authentication system may automatically turn the knob 264, or may open the door 262 automatically, or may control the door 262 such that the door 262 is opened with a light push.

The authentication system can thus assist the movement of users in addition to authenticating users.

Tenth Embodiment

A tenth embodiment of this invention is an application to a probe type authentication device.

Figure 20B:
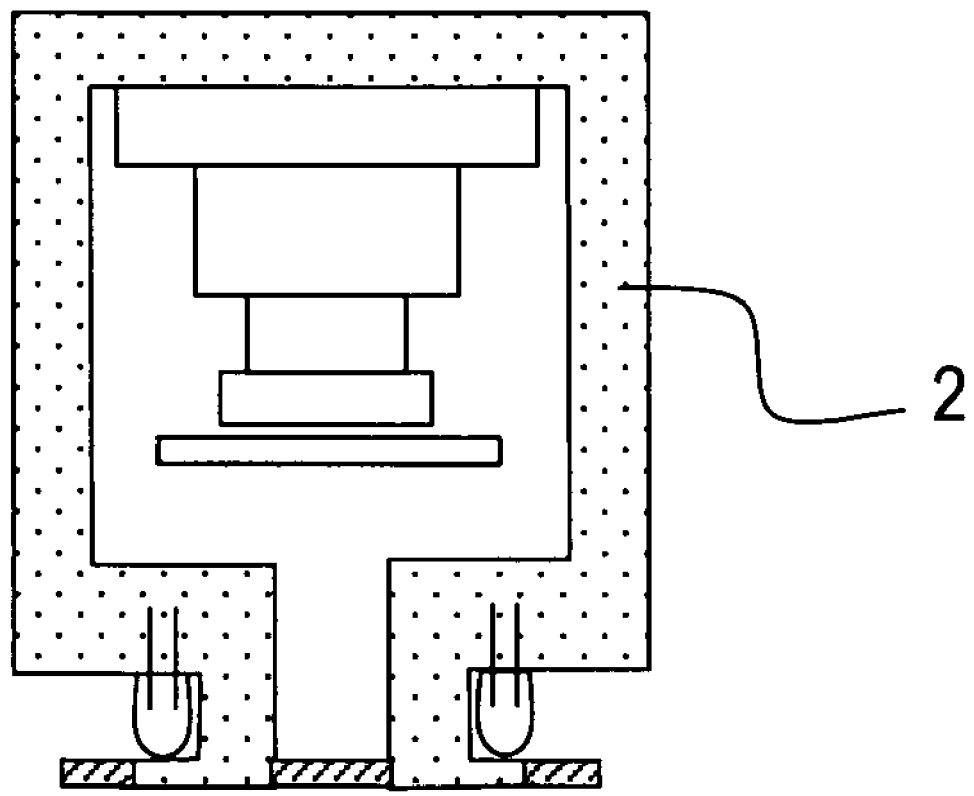
FIG. 20B is a side view of an input device that is applied to the probe type authentication device according to the tenth embodiment of this invention.

FIG. 20A shows a probe type authentication device according to the tenth embodiment of this invention. FIG. 20B is a side view of the input device 2 that is mounted to the probe type authentication device according to the tenth embodiment of this invention.

The probe type authentication device performs authentication with a probe 282 which is brought into contact with a part of the body.

The probe 282 is mounted with an authentication system, which can be any one of the authentication systems of the first to sixth embodiments.

The authentication system mounted to the probe 282 has the same configuration as the authentication system of the first embodiment (FIG. 1) except for the input device 2. The authentication system mounted to the probe 282 performs the same processing as the authentication system of the first embodiment (FIG. 7 and others). Descriptions on the common configuration and processing will be omitted.

The probe 282 is pressed against a part of the body, thereby enabling the authentication system to pick up a finger vein pattern image of the site. The probe 282 can be pressed against any part of the body including a finger (a palm side face, a nail side face, side faces, a fingertip), a palm, the back of a hand, a wrist, an arm, a foot, a face, an ear and a cheek.

The probe type authentication device can use vein patterns on any site of the body for individual authentication. With the probe type authentication device, information on a body part registered in advance in the authentication system also serves as a code, and more solid security is achieved.

The probe type authentication device may perform a vein pattern crosscheck after identifying the body part.

To be specific, the probe type authentication device stores in advance body site information in association with registered authentication data. When conducting authentication, the probe type authentication device identifies a body part whose image is picked up by the image pickup device 29.

For instance, a user may enter information about what body part has been photographed to the probe type authentication device via the input unit 16. Alternatively, the probe type authentication device may calculate a feature amount from an image picked up by the image pickup device 29 to identify the body part from the calculated feature amount. Another way to identify what body part has been photographed is to perform common image processing on images of surroundings of the body part whose image has been picked up by the image pickup device 29.

The probe type authentication device carries out a vein pattern crosscheck only when the identified body part matches the registered body site information. In other words, the probe type authentication device does not execute crosschecking processing when the identified body part does not match the registered body site information.

The probe type authentication device thus avoids erroneous authentication that vein patterns on different sites are compared with each other, and is enhanced in accuracy of authentication.

Combining one of the second to fifth embodiments of this application with the first embodiment or the sixth embodiment is naturally within a range disclosed by this application.

It is also possible to combine the configurations of the first to sixth embodiments with one of the seventh to tenth embodiment suitably as long as there are no contradictions.

INDUSTRIAL APPLICABILITY

This invention is applicable to individual authentication devices used in PCs, portable terminals, ATMs, automobiles, room access management and the like.

The invention claimed is:

1. A vein authentication device comprising:
   an interface on which a part of a living body whose image is to be picked up is placed;
   one or more light sources for emitting infrared light;
   an image pickup unit for picking up a blood vessel image of the part of the living body using infrared light emitted from the light sources;
   an image computing unit for processing the blood vessel image picked up by the image pickup unit; and
   a light shielding unit for shielding infrared light emitted from the light sources and preventing the infrared light from traveling in an image pickup direction of the image pickup unit,
   wherein the interface has an opening opened in the image pickup direction of the image pickup unit, and
   wherein the light sources irradiates the part of the living body with infrared light from an image pickup side of the part of the living body.

2. The vein authentication device according to claim 1, wherein the part of the living body is a finger.

3. The vein authentication device according to claim 2, wherein the plural light sources line up in a direction substantially perpendicular to a longitudinal direction of a finger put on the interface.

4. The vein authentication device according to claim 2, wherein the interface is provided with plural pits extending in a longitudinal direction of a finger put on the interface.

5. The vein authentication device according to claim 2, wherein the interface has a shape concaved in the center.

6. The vein authentication device according to claim 1,
   wherein the interface allows the part of the living body to move thereon;
   wherein the image pickup unit picks up plural vein images of the part of the living body at different sites; and
   the image computing unit composites the plural vein images picked up by the image pickup unit.

7. The vein authentication device according to claim 6, further comprising a movement amount measuring unit for measuring a movement amount of the part of the living body, and
   wherein the image computing unit composites the plural vein images picked up by the image pickup unit with reference to the movement amount measured by the movement amount measuring unit.

8. The vein authentication device according to claim 1, further comprising a light amount adjusting unit for adjusting a light amount of the light sources.

9. The vein authentication device according to claim 8,
   wherein the image pickup unit picks up plural vein images of the part of the living body at different light amounts adjusted by the light amount adjusting unit; and
   the image computing unit composites the plural images picked up by the image pickup unit.

10. The vein authentication device according to claim 1, wherein the interface is formed integrally with the light shielding unit.

11. A vein authentication device, comprising:
    an interface on which a part of a living body whose image is to be picked up is placed;
    one or more light sources for emitting infrared light;
    an image pickup unit for picking up a vein image of the part of the living body using infrared light emitted from the light sources;
    an image computing unit for processing the vein image picked up by the image pickup unit, and in that; and
    a light shielding unit for shielding infrared light emitted from the light sources,
    wherein the interface has an opening opened in an image pickup direction of the image pickup unit,
    wherein the light sources is placed laterally to the opening,
    wherein the light sources emits infrared light having an optical axis in the image pickup direction to irradiate the part of the living body with infrared light from an image pickup side of the part of the living body, and
    wherein the light shielding unit is provided between the opening and the light sources, and to more than half of an upper portion of the light sources on the opening side.

12. A vein authentication device, comprising:
    an image pickup unit for picking up a vein image;
    an image computing unit for processing the vein image picked up by the image pickup unit;
    an interface on which a part of a living body whose image is to be picked up is placed;
    one or more light sources for emitting infrared light; and
    a light shielding unit for shielding infrared light emitted from the light sources,
    wherein the interface has an opening opened in an image pickup direction of the image pickup unit,
    wherein the light sources is placed laterally to the opening,
    wherein the light sources emits infrared light having an optical axis that is tilted in a direction opposite to the opening to irradiate the part of the living body with infrared light from an image pickup side of the part of the living body, and
    wherein the light shielding unit is provided between the opening and the light sources, and to an upper portion of the light sources on the opening side.

* * * * *